(12) United States Patent
Doyle et al.

(10) Patent No.: US 8,277,782 B2
(45) Date of Patent: Oct. 2, 2012

(54) TOPICAL ORAL CARE COMPOSITIONS COMPRISING HOST RESPONSE MODULATING AGENTS

(75) Inventors: Matthew Joseph Doyle, Cincinnati, OH (US); Stephen Joseph Hunter-Rinderle, Mason, OH (US); Robert Ernest Singer, Jr., Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 11/409,850

(22) Filed: Apr. 24, 2006

(65) Prior Publication Data
US 2006/0193790 A1    Aug. 31, 2006

Related U.S. Application Data

(63) Continuation of application No. 09/607,602, filed on Jun. 30, 2000, now abandoned.

(51) Int. Cl.
*A61K 7/16* (2006.01)
(52) U.S. Cl. .................................... 424/49; 424/58
(58) Field of Classification Search .................. 424/49, 424/58
See application file for complete search history.

(56) References Cited

U.S. PATENT DOCUMENTS

| | | | |
|---|---|---|---|
| 4,599,228 A | 7/1986 | Ladanyi | |
| 5,147,632 A * | 9/1992 | Pan et al. | 424/54 |
| 5,204,089 A * | 4/1993 | Hara et al. | 424/58 |
| 5,258,173 A * | 11/1993 | Waterfield | 424/49 |
| 5,294,433 A | 3/1994 | Singer et al. | |
| 5,356,615 A | 10/1994 | Gaffar | |
| 5,364,616 A * | 11/1994 | Singer et al. | 424/52 |
| 5,409,692 A * | 4/1995 | Nakahara et al. | 424/49 |
| 5,431,927 A | 7/1995 | Hand et al. | |
| 5,451,401 A * | 9/1995 | Zerby et al. | 424/57 |
| 5,464,609 A | 11/1995 | Kelm et al. | |
| 5,470,565 A * | 11/1995 | Hayakawa et al. | 424/52 |
| 5,578,293 A | 11/1996 | Prencipe et al. | |
| 5,639,746 A | 6/1997 | Yelm | |
| 5,646,174 A | 7/1997 | Kelm et al. | |
| 5,656,591 A | 8/1997 | Tomita et al. | |
| 5,672,598 A | 9/1997 | De et al. | |
| 5,753,217 A | 5/1998 | Christopfel | |
| 5,766,622 A * | 6/1998 | Nelson | 424/440 |
| 5,780,046 A | 7/1998 | Humber et al. | |
| 5,785,951 A | 7/1998 | Kelm et al. | |
| 5,830,511 A | 11/1998 | Mullerat et al. | |
| 5,830,915 A | 11/1998 | Pikul et al. | |
| 5,875,798 A | 3/1999 | Petrus | |
| 5,875,799 A | 3/1999 | Petrus | |
| 5,906,811 A * | 5/1999 | Hersh | 424/54 |
| 5,945,087 A | 8/1999 | Nelson et al. | |
| RE36,419 E | 11/1999 | Cavanaugh, Jr. | |
| 6,004,587 A | 12/1999 | Mullerat et al. | |
| 6,015,912 A | 1/2000 | Wang et al. | |
| 6,025,326 A * | 2/2000 | Steinberg et al. | 514/2 |
| 6,228,347 B1 * | 5/2001 | Hersh | 424/49 |
| 6,235,269 B1 * | 5/2001 | Witt et al. | 424/53 |
| 6,350,438 B1 * | 2/2002 | Witt et al. | 424/53 |
| 6,814,958 B1 * | 11/2004 | Sekimoto | 424/58 |
| 2007/0154414 A1 * | 7/2007 | Bonfiglio | 424/58 |

FOREIGN PATENT DOCUMENTS

| | | |
|---|---|---|
| CN | 1075868 | 9/1993 |
| CN | 1213534 | 4/1995 |
| CN | 1103776 | 6/1995 |
| CN | 1109742 | 10/1995 |
| EP | 0 430 474 | 6/1991 |
| GB | 2 290 233 | 12/1995 |
| JP | 04 089428 A | 3/1992 |
| JP | 06 305945 A | 11/1994 |
| JP | 11 139947 | 5/1999 |
| WO | WO 97/16159 | 5/1997 |
| WO | WO 97/47292 | 12/1997 |
| WO | WO 98/08814 | 3/1998 |
| WO | WO 98/08815 | 3/1998 |
| WO | WO 98/08822 | 3/1998 |
| WO | WO 98/08823 | 3/1998 |
| WO | WO 98/08825 | 3/1998 |
| WO | WO 98/17195 | 4/1998 |
| WO | WO 98/17237 | 4/1998 |
| WO | WO 98/17270 | 4/1998 |
| WO | WO 99/06340 | 2/1999 |

OTHER PUBLICATIONS

Phytochemicals: Epigallocatechin Gallate. www.phytochemicals.com Sep. 2007.*

(Continued)

*Primary Examiner* — Ralph Gitomer

(57) ABSTRACT

The present invention relates to topical oral care compositions comprising in a pharmaceutically acceptable carrier a safe and effective amount of a host-response modulating agent including one or more of an anti-oxidant and modifier of cell redox status, anti-inflammatory agent, metalloproteinase inhibitor, vitamins and nutrients key to maintenance of a host response balance and inhibitor of activation of NF-kB in combination with one or a mixture of additional oral therapeutic actives selected from antimicrobial/antiplaque agents, biofilm inhibiting agents, antibiotics; analgesics and local anesthetic agents; dentinal desensitizing agents and odor masking agents. The present compositions are effective in treating and preventing bacteria-mediated diseases present in the oral cavity and in mediating host reaction to the presence of pathogenic bacteria in the oral cavity as well as the toxins and endotoxins, inflammatory cytokines and mediators released or prompted by these oral pathogens. By controlling bacteria-mediated diseases and conditions present in the oral cavity and modulating host reaction, spread into the bloodstream and other parts of the body of pathogenic bacteria and associated harmful substances is prevented or minimized.

2 Claims, No Drawings

OTHER PUBLICATIONS

Bullon B. et al. Oxidative Injury and Inflammatory Periodontal Diseases. Critical Reviews in Oral Biology and Medicine. 10(4)458-476, 1999.*

Hattori M. et al. Effect of Tea Polyphenols on glucan Synthesis by Glucosyltransferase from *S. mutans*. Chem Pharm Bull 38(3)717-720, 1990.*

U.S. Appl. No. 09/607,602, filed Jun. 30, 2000, Doyle et al.

Deriso, A.J., et al., "Chlorhexidine Gluconate 0.12% Oral Rinse Reduces the Incidence of Total Nosocmial Respiratory Infection and Nonprophylactic Systemic Antibiotic Use in Patients Undergoing Heart Surgery," Chest, Jun. 1996, pp. 1556-1561, vol. 109.

Grossi, S.G., et al., "Treatment of Periodontal Disease in Diabetics Reduces Glycated Hemoglobin," Journal of Periodontology, Aug. 1997, pp. 713-719., vol. 68.

Limeback, H., "Implication of Oral Infections on Systemic Diseases in the Instituionalized Elderly with a Special Focus on Pneumonia," Annals of Periodontology, Jul. 1998, pp. 162-175, vol. e.

Miller, L. S., et al., "The Relationships Between Reduction in Periodontal Inflammation and Diabetes Control: A Report of 9 Cases," Journal of Periodontology, Oct. 1992, pp. 843-848, vol. 63.

Williams, R. C., et al., Periodontology 2000, vol. 23, Jun. 2000, pp. 9-12, vol. 23.

* cited by examiner

TOPICAL ORAL CARE COMPOSITIONS COMPRISING HOST RESPONSE MODULATING AGENTS

CROSS REFERENCE TO RELATED APPLICATION

This application is a continuation of U.S. application Ser. No. 09/607,602, filed on Jun. 30, 2000 now abandoned.

FIELD OF THE INVENTION

The present invention relates to promoting and/or enhancing whole body health or overall systemic health in humans and other animals, by use of topical oral compositions comprising one or a mixture of host-response modulating agents, which are particularly effective in mediating host reaction to the presence of periodontal pathogens in the oral cavity as well as the toxins and endotoxins released by these pathogens and the inflammatory cytokines and mediators prompted by these pathogens. More particularly, the present invention relates to methods of using the present compositions to reduce the risk in the development of cardiovascular disease, stroke, atherosclerosis, diabetes, severe respiratory infections, premature births and low birth weight, and associated increased risk of mortality, by treating and preventing diseases and conditions of the oral cavity.

BACKGROUND OF THE INVENTION

Recent research has revealed that periodontal disease (gum disease) may be a far more serious threat to overall systemic health than previously realized. Periodontitis, a form of periodontal disease, is a tissue destructive process resulting from the accumulation of pathogenic bacteria along the gingival margin and the consequent tissue destructive host response to these pathogens. The presence of periodontitis can result in the release of bacteria and/or bacterial toxins into the bloodstream. The host responses to the presence of these bacterial pathogens and/or toxins in the bloodstream may contribute to the development of atherosclerosis (heart disease), increase the risk of premature, underweight babies; and pose a serious threat to people whose health is compromised by diabetes, severe respiratory diseases, stroke and bacteremia (bacteria in the blood).

For a long time, it has been known that bacteria may affect the heart. Now evidence is mounting that suggests people with periodontitis, a bacterial-mediated disease, may be more at risk for heart disease, and have a significantly higher risk of having a fatal heart attack, than patients without periodontitis. Heart disease is the leading cause of death in most developed countries, and periodontitis disease is one of the most common bacterial-mediated diseases in humans, affecting as many as one third of those over 50. Thus even if periodontitis has only a modest effect on increasing the risk of heart attack, its prevalence may make it a significant contributor to the risk for heart disease in the population as a whole.

Several theories exist to explain the link between periodontal disease and heart disease. One theory is that oral bacterial pathogens enter the blood through inflamed gums, attach to fatty plaques in the coronary arteries (heart blood vessels) and cause small blood clots that contribute to clogged arteries. Researchers have found that 70% of the fatty plaque that blocks carotid arteries and causes stroke contains bacteria. Forty percent of those bacteria have been traced to the mouth. Coronary artery disease is characterized by a thickening of the walls of the coronary arteries due to the buildup of fatty proteins. Blood clots can obstruct normal blood flow, restricting the amount of nutrients and oxygen required for the heart to function properly. This may lead to heart attacks. Another possibility is that changes in systemic inflammatory mediators caused by periodontitis increase development of atherosclerotic plaque, which then contributes to thickening of the arterial walls.

Research also suggests that people with diabetes are more likely to have periodontitis than people without diabetes, and the presence of periodontitis may make it more difficult for diabetics to control their blood sugar. It is known that the presence of periodontitis can increase blood sugar, contributing to increased periods of time when the body functions with a high blood sugar, which puts a diabetic person at increased risk for diabetic complications. Thus, controlling periodontitis may help control diabetes. A recent study ("Heightened Gingival Inflammation and Attachment Loss in Type 2 Diabetics with Hyperlipidemia," in Journal of Periodontology, November, 1999) found that poorly controlled type 2 diabetic patients are more likely to develop periodontal disease than well-controlled diabetics. In addition, the study further explains why diabetics are more susceptible to severe periodontal disease. The study concluded that poorly controlled diabetics respond differently to bacterial plaque at the gum line than well-controlled diabetics and non-diabetics, possibly due to elevated serum triglycerides. Poorly controlled diabetics have more harmful proteins (cytokines) in their gingival tissue, causing destructive inflammation of the gums. In turn beneficial proteins (growth factors) are reduced, interfering with the healing response to infection. "Increased serum triglyceride levels in uncontrolled diabetics seem to be related to greater attachment loss and probing depths, which are measures of periodontal disease," said Christopher Cutler, D.D.S., Ph.D., the study's lead researcher.

Evidence is also mounting that suggests pregnant women who have periodontitis may be significantly more likely to have a premature, low-birthweight baby. The inflammatory response prompted by periodontitis and/or the associated presence of bacterial pathogens/toxins in the bloodstream are cause for concern among pregnant women because they pose a risk to the health of the fetus. The presence of periodontitis appears to retard fetal growth by releasing into the woman's bloodstream bacterial toxins that reach the placenta and interfere with fetal development by increasing systemic levels of inflammatory mediators that could prompt pre-term birth. Scientists have also proposed that the presence of a low-grade infection may influence harmed cells to discharge inflammatory chemicals, similar to those used to induce abortion, that can cause the cervix to dilate and set off uterine contractions. The risk of having a premature baby of low birth weight was estimated to be at least 7.5 times as high for women with severe periodontal disease, and to occur in 5 percent of pregnancies, costing the U.S. $5.7 billion a year. [Offenbacher S, J. Periodontol. 1996 October;67(10 Suppl): 1103-13].

Research further suggests that periodontal disease may pose an increased risk for severe respiratory diseases like pneumonia, bronchitis, emphysema and chronic obstructive pulmonary disease.

The VA Dental Longitudinal Study (DLS) and Normative Aging Study (NAS) examined the relationship of periodontal disease to mortality from all outcomes and concluded that periodontal status at baseline was a significant and independent predictor of mortality. [Annals of Periodontology, 3(1), 339-49, July 1998] The study was conducted starting in the mid-1960s among men on good medical health and followed over more than a 25-year period. It was found that for each 20% increment in mean whole-mouth ABL (alveolar bone loss, measured with a Schei ruler using full-mouth series of periapical films), the subject's risk of death increased by 51%. The risk of death was also found to be associated with periodontal status as measured clinically by periodontal probing depth. Subjects in the population group with the deepest average probing depths were found to be at 74% higher risk.

According to Dr. Michael Roizen, University of Chicago internist and anesthesiologist, keeping teeth and gums healthy adds 6.4 years to a person's life. Indeed, the American Academy of Periodontology (AAP) concurs that keeping teeth and gums healthy ranks right up there with taking vitamins, quitting smoking and reducing stress as one of the top things that a person can do to add years to life.

Periodontal disease ("gum disease") is a broad term used to describe those diseases which attack the gingiva and the underlying alveolar bone supporting the teeth. The disease exists in a number of species of warm blooded animals such as humans and canines, and includes a series of diseases exhibiting various syndromes which vary from each other according to the stage or situation of the disease or the age of the patient. The term is used for any inflammatory disease which initially occurs at a marginal gingiva area and may affect the alveolar bone. Periodontal disease affects the periodontium, which is the investing and supporting tissue surrounding a tooth (i.e., the periodontal ligament, the gingiva, and the alveolar bone). Two common periodontal diseases are gingivitis (inflammation of the gingiva) and periodontitis (inflammation of the periodontal ligament manifested by progressive resorption of alveolar bone, increasing mobility of the teeth, and loss of the teeth at advanced stage). Combinations of inflammatory and degenerative conditions are termed periodontitis complex. Other terms used for various aspects of periodontal disease are "juvenile periodontitis", "acute necrotizing ulcerative gingivitis", and "alveolar pyorrhea".

Periodontal disease may involve one or more of the following conditions: inflammation of the gingiva, formation of periodontal pockets, bleeding and/or pus discharge from the periodontal pockets, resorption of alveolar bone, loose teeth and loss of teeth. Periodontal disease is generally considered to be caused by/associated with bacteria which are generally present in dental plaque which forms on the surface of the teeth and in the periodontal pocket. Thus, known methods for treating periodontal disease often include the use of antimicrobials and/or anti-inflammatory drugs.

Alveolar bone resorption is a loss of osseous tissue from the specialized bony structure which supports the teeth. Such resorption has many causes including, but not limited to, natural remodeling following tooth extraction, osseous surgery, periodontal flap surgery, dental implants, scaling and root planing and the progression of periodontal disease.

Periodontal disease is a major cause of tooth loss in adult humans. Tooth loss from periodontal disease is a significant problem beginning at age 35, but even by age 15 it is estimated that about 4 out of 5 persons already have gingivitis and 4 out of 10 have periodontitis. While good oral hygiene, as achieved by brushing the teeth with a cleansing dentifrice, may help reduce the incidence of periodontal disease, it does not necessarily prevent or eliminate its occurrence. This is because microorganisms contribute to both the initiation and progress of periodontal disease. Thus, in order to prevent or treat periodontal disease, these microorganisms must be suppressed by some means other than simple mechanical scrubbing. Towards this end, there has been a great deal of research aimed at developing therapeutic dentifrices, mouthwashes, and methods of treating periodontal disease which are effective in suppressing these microorganisms.

Additionally research has focused on oral care compositions comprising agents such as anti-inflammatory agents. The destruction of periodontal tissue is primarily caused by the indirect effects mediated by the host's reaction to the bacteria in the periodontium and gingival sulcus. Bacterial metabolites induce leukocyte chemotaxis which results in the accumulation of inflammatory cells at the site of the bacterial challenge. Furthermore, bacterial metabolites induce the production of inflammatory mediators by leukocytic cells, in particular monocytes. Amongst these are local disease mediators such as metabolites of arachidonic acid, e.g. leukotrienes, prostaglandins and thromboxanes. Prostaglandins have been found to be particularly important in the metabolism and destruction of tissue and alveolar bone. Indeed, the production of prostaglandins in the periodontal tissues has been found to be an important mediator of the loss of alveolar bone in the periodontium; patients with periodontal breakdown show an elevated prostaglandin $E_2$ level both in the gingival tissue as well as in the crevicular fluid. Prostaglandins and thromboxanes are formed from arachidonic acid by an enzyme cascade, the first step of which is the cyclo-oxygenation by an enzyme called cyclo-oxygenase. Inhibiting the cyclo-oxygenase would inhibit the formation of prostaglandins and thus reduce alveolar bone loss, and indeed certain cyclo-oxygenase inhibitors, particularly non steroidal anti-inflammatory drugs such as indomethacin and flurbiprofen have been found to markedly reduce the resorption of alveolar bone.

However, as concluded by R. C. Williams and S. Offenbacher in Periodontology 2000, vol. 23, pp. 9-12 (June, 2000), no studies have yet demonstrated the beneficial effects of periodontal therapy on systemic disease outcomes. The authors further report that no periodontal treatment protocols are available that are specifically designed to improve systemic health.

It has now been discovered by the present inventors that topical oral compositions comprising one or a mixture of host-response modulating agents, are effective in promoting and/or enhancing whole body health in humans and in other animals. The present invention therefore relates to topical oral compositions comprising one or more host-response modulating agents and methods of use of these topical oral compositions to promote and/or enhance whole body health in humans and other animals.

As mentioned above, none of the foregoing references has disclosed or suggested the use of periodontal therapy compositions by topical application to the oral cavity to promote whole body health in humans and other animals. U.S. Pat. Nos. 5,875,798 and 5,875,799, both issued Mar. 2, 1999 to Petrus disclose toothpick and dental floss, respectively, impregnated or coated with zinc salts. The zinc containing toothpick and floss formulations are taught to be useful in treating systemic disease via absorption through periodontal tissue of zinc ions into the bloodstream in amounts sufficient to treat the systemic disease. Commonly-owned WO 97/47292, WO 98/17237 and WO 98/17270 relate to methods of preventing or controlling colds and similar maladies, such as flu, through the use of an oral composition applied to the gingival or oral mucosal tissue of subjects susceptible to colds. The oral compositions disclosed in these co-pending applications contain an H2-antagonist, stannous gluconate, and zinc citrate salt, respectively as the active ingredient. U.S. Pat. Nos. 5,830,511 and 6,004,587, Mullerat, et al., both disclose methods of systemic administration to food animals (such as chickens, turkeys and pigs), of pH-buffered redox-stabilized compositions comprising halide and oxyhalide ions, specifically via the drinking water of the animals. The compositions are said to form free radical oxyhalide intermediates that produce immunostimulatory effects in the animals, which result in their increased ability to fight off possible infections, increased feed utilization, lower mortality, decreased nitrogen excretion and overall enhanced health. All of these references are incorporated herein in their entirety.

SUMMARY OF THE INVENTION

The present invention relates to promoting whole body health in humans and animals by using topical oral compositions comprising a safe and effective amount of a host-response modulating agent in admixture with a pharmaceutically acceptable carrier, said compositions being effective in mediating host reaction to the presence of periodontal pathogens in the oral cavity as well as the toxins and endotoxins released by these pathogens and the inflammatory cytokines and mediators prompted by these oral pathogens.

DETAILED DESCRIPTION OF THE INVENTION

The present invention involves promoting whole body health in humans and animals by use of topical oral compositions comprising a safe and effective amount of a host-response modulating agent in admixture with a pharmaceutically acceptable carrier, said compositions being effective in mediating host reaction to bacterial pathogens present in the oral cavity and to the toxins and endotoxins released by these oral pathogens as well as the inflammatory cytokines and mediators prompted by these pathogens. The present invention also encompasses methods of use of these compositions comprising topically applying to the oral cavity, a safe and effective amount of a host-response modulating agent. Preferably the host-response modulating agent is selected from the group consisting of H2-antagonists; anti-inflammatory agents (including cyclo-oxygenase inhibitors and lipoxygenase inhibitors); metalloproteinase inhibitors; anti-oxidants and modifiers of cell redox status; inhibitors of activation of NF-kB; vitamins and nutrients key to maintenance of a host response balance; and mixtures thereof.

By "whole body health" as used herein is meant overall systemic health characterized by a reduction in risk of development of major systemic diseases and conditions including cardiovascular disease, stroke, diabetes, severe respiratory infections, premature births and low birth weights (including post-partum dysfunction in neurologic/developmental function), and associated increased risk of mortality.

By "diseases and conditions of the oral cavity," as used herein, is meant diseases of the oral cavity including periodontal disease, gingivitis, periodontitis, periodontosis, adult and juvenile periodontitis, and other inflammatory conditions of the tissues within the oral cavity, plus caries, necrotizing ulcerative gingivitis, resulting conditions from these diseases such as oral or breath malodor, and other conditions such as herpetic lesions, and infections that may develop following dental procedures such as osseous surgery, tooth extraction, periodontal flap surgery, dental implantation, and scaling and root planing. Also specifically included are dentoalveolar infections, dental abscesses (e.g., cellulitis of the jaw; osteomyelitis of the jaw), acute necrotizing ulcerative gingivitis (i.e., Vincent's infection), infectious stomatitis (i.e., acute inflammation of the buccal mucosa), and Noma (i.e., gangrenous stomatitis or cancrum oris). Oral and dental infections are more fully disclosed in Finegold, Anaerobic Bacteria in Human Diseases, chapter 4, pp 78-104, and chapter 6, pp 115-154 (Academic Press, Inc., NY, 1977), the disclosures of which are incorporated herein by reference in their entirety.

The compositions and methods of treatment of the present invention are particularly effective for treating or preventing periodontal disease (gingivitis and/or periodontitis) and resulting breath malodor.

By "topical oral compositions" as used herein means a product which in the ordinary course of usage is not intentionally swallowed for purposes of systemic administration of particular therapeutic agents, but is rather retained in the oral cavity for a time sufficient to contact substantially all of the dental surfaces and/or oral tissues for purposes of oral activity.

By "safe and effective amount" as used herein means sufficient mount of material to provide the desired benefit while being safe to the hard and soft tissues of the oral cavity. The safe and effective amount of host response modulating agent, will vary with the particular condition being treated, the age and physical condition of the patient being treated, the severity of the condition, the duration of treatment, the nature of concurrent therapy, the specific form of the host response modulating agent employed, and the particular vehicle from which the host response modulating agent ion is applied.

By the term "comprising", as used herein, is meant that various additional components can be conjointly employed in the compositions of this invention as long as the listed materials perform their intended functions.

By the term "carrier", as used herein, is meant a suitable vehicle (including excipients and diluents), which is pharmaceutically acceptable and can be used to apply the present compositions in the oral cavity.

By "dentifrice" as used herein is meant toothpaste, tooth powder, and tooth gel formulations unless otherwise specified.

In a preferred method, the present compositions are used to treat and prevent diseases and conditions of the oral cavity including periodontal disease, thereby promoting and enhancing whole body health for the individual being treated, as evidenced by the following health indices (or biomarkers):

1) reduction in risk of development of heart attack, stroke, diabetes, severe respiratory infections, low birth weight infants, post-partum dysfunction in neurologic/developmental function, and associated increased risk of mortality;
2) reduction in the development of fatty arterial streaks, atherosclerotic plaques, progression of plaque development, thinning of the fibrous cap on atherosclerotic plaques, rupture of atherosclerotic plaques, and the subsequent blood clotting events;
3) reduction in carotid arterial (intimal) wall thickness (e.g., as assessed by ultra-sound techniques)
4) reduction in exposure of blood and systemic circulation to oral pathogens and/or their toxic components, specifically leading to reduction in blood levels of oral bacteria, lipopolysaccharide (LPS) and/or the incidence of oral pathogens and/or components thereof found in arterial plaques, arterial structures, and/or distant organs (e.g., heart, liver, pancreas, kidney);
5) reduction in the exposure of the lower respiratory track to the inhalation of bacterial pathogens and the subsequent development of pneumonias and/or exacerbation of chronic obstructive lung disease;
6) reduction in alterations in circulating hematocrit, hemoglobin, white blood cell count and/or platelet counts;
7) reduction in the incidence of disregulation in blood/serum levels of inflammatory mediators/cytokines such as TNF-α, IL-6, CD-14, and IL-1;

8) reduction in the incidence of disregulation of blood/serum levels of acute phase reactants including C-reactive protein, fibrinogen, α1-antitrypsin, and haptoglobin;
9) reduction in the incidence of disregulation of blood/serum markers of metabolic disregulation including homocysteine, glycosylated hemoglobin, 8-iso-PGF-2alpha, and uric acid;
10) reduction in incidence of disregulation of glucose metabolism as typically assessed by impaired glucose tolerance test, increased fasting blood glucose levels, and abnormal fasting insulin levels; and
11) reduction in disregulation of blood lipid levels specifically including blood or serum cholesterol, triglycerides, LDL, HDL, VLDL, Apolipoprotein B, and/or Apolipoprotein A-1.

Without wishing to be bound by theory, it is believed that the present compositions promote overall body health by effectively modulating the body's response to pathogenic oral bacteria, associated bacterial toxins and endotoxins, and inflammatory mediators and cytokines prompted by these pathogenic bacteria. The present compositions are effective in treating and preventing bacterial-mediated diseases present in the oral cavity, such as plaque, gingivitis, periodontitis, and herpetic lesions, as well as infections that may develop following dental procedures such as osseous surgery, tooth extraction, periodontal flap surgery, dental implantation, and scaling and root planing. By controlling bacterial-mediated diseases and conditions present in the oral cavity, spread into the bloodstream and other parts of the body of pathogenic bacteria and associated harmful substances including toxins and endotoxins is prevented or minimized.

It is believed that oral infections could lead to systemic infection. Bacteria can spread from the mouth into the bloodstream and other parts of the body, putting a person's health at risk. Recent research has found that periodontitis may contribute to the development of a number of serious conditions including heart disease, diabetes, severe respiratory diseases and premature, underweight births.

It is now known that chronic oral cavity infection produces a biologic burden of bacterial toxins and inflammatory cytokines that may initiate and exacerbate atherosclerosis and thromboembolic events. Additionally, a known periodontal pathogen, *Porphyromonas gingivalis* has been isolated from arteriosclerotic plaques. Periodontal disease has also been shown to induce episodes of significant bacteremias and thromboembolic events such as myocardial infarction; stroke can occur following bacteremia. Certain bacteria associated with oral cavity diseases, *Streptococcus sanguis* and *Porphyromonas gingivalis*, have been demonstrated to cause platelets to aggreggate upon contact with these bacteria. The resultant bacterially-induced platelet agggregates can form the emboli which are responsible for the acute myocardial infarction or stroke.

Periodontitis, a common form of periodontal disease, is believed to be caused by a small group of Gram-negative bacteria present on the tooth root surfaces as biofilms. Biofilms are defined as "matrix-enclosed bacterial populations adherent to each other and/or to surfaces or interfaces". Experts have recently concluded that three species, all of which are Gram-negative and anaerobic, are present in these biofilms and account for most cases of periodontitis. These are *Porphyromonas gingivalis, Bacteroides forsythus* and *Actinobacillus actinomycetemcomitans*, with the latter found mostly in cases of juvenile periodontitis. The bacteria in the biofilms shed vesicles that are rich in lipopolysaccharides (LPS). Bacteria and bacterial substances, especially LPS, traverse the junctional and pocket epithelium to gain access to connective tissue and blood vessels, initiate and perpetuate immunoinflammation. All of the components of blood and serum pass into the connective tissue. B- and T-lymphocytes, plasma cells and macrophages appear in the periodontal tissues. LPS interacts with monocytes and macrophages to activate cells to synthesize large quantities of proinflammatory cytokines (including IL-1, TNFα, PGE$_2$) and matrix metalloproteinases (MMP's). MMP's destroy the connective tissues of the gingiva and periodontal ligament; IL-1, TNFα, and PGE$_2$ have been shown to mediate bone destruction. Periodontitis may enhance susceptibility to systemic diseases in several ways. LPS and viable Gram-negative bacteria from the biofilms and cytokines from the inflamed periodontal tissues may enter the circulation in pathogenic quantities.

In one aspect the present invention relates to topical oral compositions for humans and other animals, including therapeutic rinses, especially mouth rinses; dentifrices such as toothpastes, tooth gels, and tooth powders; non-abrasive gels; chewing gums; mouth sprays; lozenges (including breath mints); dental solutions (including irrigation fluids); dental implements (such as dental floss and tape), and pet care products (including nutritional supplements, food, drinking water additives, chews or toys), comprising:

(a) a safe and effective amount, preferably a minimally effective amount, of a host-response modulating agent; and (b) a pharmaceutically-acceptable topical, oral carrier;

wherein the host-response modulating agent is selected from the group consisting of H2-antagonists; anti-inflammatory agents (including cyclo-oxygenase inhibitors and lipoxygenase inhibitors); metalloproteinase inhibitors; anti-oxidants and modifiers of cell redox status; inhibitors of activation of NF-kB; and vitamins and nutrients key to maintenance of a host response balance; and mixtures thereof.

Host-Response Modulating Agents

The present invention includes a host-response modulating agent as an essential ingredient in the compositions and methods of the present invention.

H-2 Antagonists

Histamine-2 (H-2 or H2) receptor antagonist compounds (H-2 antagonists) may be used in the oral care composition of the present invention. As used herein, selective H-2 antagonists are compounds that block H-2 receptors, but do not have meaningful activity in blocking histamine-1 (H-1 or H1) receptors. Selective H-2 antagonists stimulates the contraction of smooth muscle from various organs, such as the gut and bronchi; this effect can be suppressed by low concentrations of mepyramine—a typical antihistaminic drug. The pharmacological receptors involved in these mepyramine-sensitive histamine responses have been defined as H-1 receptors (Ash, A. S. F. & H. O. Schild, Brit. J. Pharmacol Chemother., Vol. 27 (1966), p. 427. Histamine also stimulates the secretion of acid by the stomach (Loew, E. R. & O. Chickering, Proc. Soc. Exp. Biol. Med., Vol. 48 (1941), p. 65), increases the heart rate (Trendelenburg, U., J. Pharmacol., Vol. 130 (1960), p. 450), and inhibits contractions in the rat uterus (Dews, P. B. & J. D. P. Graham, Brit. J. Pharmacol. Chemother., Vol. 1 (1946), p. 278); these actions cannot be antagonized by mepyramine and related drugs. The H-2 antagonists useful in the oral care compositions or substances are those that blockade the receptors involved in mepyramine-insensitive, non-H-1 (H-2), histamine responses, and do not blockade the receptors involved in mepyramine-sensitive histamine responses.

Selective H-2 antagonists are those compounds found to be H-2 antagonists through their performance in classical preclinical screening tests for H-2 antagonist function. Selective H-2 antagonists are identified as compounds which can be demonstrated to function as competitive or non-competitive inhibitors of histamine-mediated effects in those screening models specifically dependent upon H-2 receptor function, but to lack significant histamine antagonist activity in those screening models dependent upon H-1 receptor function. Specifically, this includes compounds that would be classified as described by Black, J. W., W. A. M. Duncan, C. J. Durant, C. R. Ganellin & E. M. Parsons, "Definition and Antagonism of Histamine H2-Receptors", Nature, Vol. 236 (Apr. 21, 1972), pp. 385-390 (Black), as H-2 antagonists if assessed as described by Black through testing with the guinea pig spontaneously beating right atria in vitro assay and the rat gastric acid secretion in vivo assay, but shown to lack in significant H-1 antagonist activity relative to H-2 antagonist activity, if assessed as described by Black with either the guinea pig ileum contraction in vitro assay or the rat stomach muscle contraction in vivo assay. Preferably selective H-2 antagonists demonstrate no significant H-1 activity at reasonable dosage levels in the above H-1 assays. Typical reasonable dosage level is the lowest dosage level at which 90% inhibition of histamine, preferably 99% inhibition of histamine, is achieved in the above H-2 assays.

Selective H-2 antagonists include compounds meeting the above criteria which are disclosed in U.S. Pat. Nos. 5,294,433 and 5,364,616 to Singer, et al., issued Mar. 15, 1994 and Nov. 15, 1994 respectively and assigned to Procter & Gamble, wherein the selective H-2 antagonist is preferably selected from the group consisting of cimetidine, etintidine, ranitidine, ICIA-5165, tiotidine, ORF-17578, lupitidine, donetidine, famotidine, roxatidine, pifatidine, lamtidine, BL-6548, BMY-25271, zaltidine, nizatidine, mifentidine, BMY-25368 (SKF-94482), BL-6341A, ICI-162846, ramixotidine, Wy-45727, SR-58042, BMY-25405, loxtidine, DA-4634, bisfentidine, sufotidine, ebrotidine, HE-30-256, D-16637, FRG-8813, FRG-8701, impromidine, L-643728, and HB-408. Particularly preferred is cimetidine (SKF-92334), N-cyano-N'-methyl-N"-(2-(((5-methyl-1H-imidazol-4-yl)methyl)thio)ethyl)guanidine:

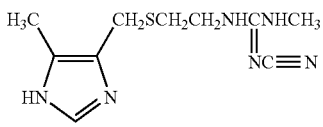

Cimetidine is also disclosed in the Merck Index, 11th edition (1989), p. 354 (entry no. 2279), and Physicians' Desk Reference, 46th edition (1992), p. 2228. Related preferred H-2 antagonists include burimamide and metiamide.

Selective H-2 antagonists include the imadazolylmethylthioethyl alkynyl guanidines meeting the above criteria which are disclosed in U.S. Pat. No. 4,112,234 issued to Crenshaw and Luke on Sep. 5, 1978. Preferred is etintidine (BL-5641, BL-5641A), N-cyano-N'-(2-(((5-methyl-1H-imidazol-4-yl)methyl)thio)ethyl)-N"-2-propynyl-guanidine.

Selective H-2 antagonists include the aminoalkyl furan derivatives meeting the above criteria which are disclosed in U.S. Pat. No. 4,128,658 issued to Price, Clitherow and Bradshaw on Dec. 5, 1978. Particularly preferred is ranitidine, especially its hydrochloride salt (AH-19065). Ranitidine is N-(2-(((5-((dimethylamino)methyl)-2-furanyl)methyl)thio)ethyl)-N'-methyl-2-nitro-1,1-ethenediamine: Ranitidine is also disclosed in the Merck Index, 11th edition (1989), p. 1291 (entry no. 8126), and Physicians' Desk Reference, 46th edition (1992), p. 1063. Related preferred compounds include hydroxymethyl ranitidine; ranitidine bismuth citrate (GR-122311, GR-122311X); and AH-18801, N-cyano-N'-(2-(((5-((dimethylamino)methyl)-2-furanyl)methyl)thio) ethyl)-N"-methyl guanidine.

Selective H-2 antagonists include the guanidine derivatives of imidazoles and thiazoles meeting the above criteria which are disclosed in U.S. Pat. No. 4,165,377 issued to Jones and Yellin on Aug. 21, 1979. Preferred is ICIA-5165, N-(4-(2-((aminoiminomethyl)amino)-4-thiazolyl)butyl)-N'-cyano-N"-methyl-guanidine.

Selective H-2 antagonists include the guanidine derivatives of imidazoles and thiazoles meeting the above criteria which are disclosed in U.S. Pat. No. 4,165,378 issued to Gilman, Wardleworth, and Yellin on Aug. 21, 1979. Preferred is tiotidine (ICI-125211), N-(2-(((2-((aminoiminomethyl)amino)A-thiazolyl)methyl)thio)ethyl)-N'-cyano-N"-methylguanidine.

Selective H-2 antagonists include the N-alkynyl-N'-(omega-((5-substituted-2-furyl)alkylthio)alkyl)-derivatives of N"-cyanoguanidine and of 1,1-diamino-2-(substituted)-ethylene compounds meeting the above criteria which are disclosed in U.S. Pat. No. 4,203,909 issued to Algieri and Crenshaw on May 20, 1980. Preferred is ORF-17578, N-(2-(((5-((dimethylamino)methyl)-2-furanyl)methyl)thio)ethyl)-2-nitro-N'-2-propynyl-, 1-ethene diamine.

Selective H-2 antagonists include the substituted pyrimidine compounds meeting the above criteria which are disclosed in U.S. Pat. No. 4,234,588 issued to Brown and Ife on Nov. 18, 1980. Preferred are lupitidine (SKF-93479), 2-((2-(((5-((dimethylamino)methyl)-2-uranyl)methyl)thio)ethyl) amino)-5-, ((6-methyl-3-pyridinyl)methyl)-4(1H)-pyrimidinone; and donetidine (SKF-3574), 5-((1,2-dihydro-2-oxo-4-pyridinyl)methyl)-2-((2-(((5-(dimethylamino)methyl)-2-furanyl)methyl)thio)ethyl)amino)-4(1H)-pyrimidinone.Also preferred are related compounds SKF-93828, 2-((2-(5-((4-(dimethylaminomethyl)-2-pyridyl)methyl)thio)ethyl) amino)-5-(2-methyl-5-pyridyl)pyrimidin-4-one; and SKF-93996, the 2-(4-(4-(dimethylaminomethyl)-2-pyridyl) butylamino) analogue of SKF 93828.

Selective H-2 antagonists include the 3-amino-5-(4-pyridyl)-1,2,4-triazole derivatives meeting the above criteria which are disclosed in U.S. Pat. No. 4,276,297 issued to Lipinski on Jun. 30, 1981. Preferred is 3-amino-5-(2-(ethylamino)-4-pyridyl)-1,2,4-triazole.

Selective H-2 antagonists include the guanidinothiazole compounds meeting the above criteria which are disclosed in U.S. Pat. No. 4,283,408 issued to Hirata, Yanagisawa, Ishii, Tsukamoto, Ito, Isoaura, and Takeda on Aug. 11, 1981. Preferred is famotidine (YM-1170, MK-208), 3-(((2-((aminoiminomethyl)amino)A-thiazolyl)methyl)thio)-N-aminosulfonyl) propanimidamide. Famotidine is also disclosed in the Merck Index, 11th edition (1989), p. 617 (entry no. 3881), and Physicians' Desk Reference, 46th edition (1992), p. 1524.

Selective H-2 antagonists include the phenoxypropylamine derivatives meeting the above criteria which are disclosed in U.S. Pat. No. 4,293,557 issued to Shibata, Itaya, Yamakoshi, Kurata, Koizumi, Tarutani, Sakuma and Konishi on Oct. 6, 1981. Preferred is roxatidine (Hoe-062, TZU-9368), 2-hydroxy-N-(3-(3-(1-piperidinylmethyl)phenoxy) propyl)-acetamide; and roxatidine acetate (pifatidine, Hoe-760, TZU-0460), 2-(acetyloxy)-N-(3-(3-(1-piperidinylmethyl)phenoxy)propyl)-acetamide: Roxatidine acetate is also disclosed in the Merck Index, 11th edition (1989), p. 1316 (entry no. 8252).

Selective H-2 antagonists include the 1,2,4-triazole-3,5-diamine derivatives meeting the above criteria which are disclosed in U.S. Pat. No. 4,318,913 issued to Clitherow, Bradshaw, Mackinnon, Price, Martin-Smith and Judd on Mar. 9, 1982. Preferred is lamtidine (AH-22216), 1-methyl-N5-(3-(3 (1-piperidinylmethyl)phenoxy)propyl)-1H-1,2,4-triazole-3, 5-diamine. Also preferred are related compounds AH-21201 and AH-21272.

Selective H-2 antagonists include the 3-(hydroxy or amino)-4-substituted amino)- and 3,4-di(substituted amino)-1,2,5-thiadiazole-1-oxides and 1,1-dioxides meeting the above criteria which are disclosed in U.S. Pat. No. 4,374,248 issued to Crenshaw and Algieri on Feb. 15, 1983. Preferred are BL-6548 (ORF-17910), N-(3-(3-((4-methyl-1-piperidinyl)methyl)phenoxy)propyl)-1,2,5-hiadiazole-3,4-diamine 1-oxide; and BMY-25271, N-(2-(((5-(dimethylamino)methyl)-2-furanyl)methyl)thio)ethyl)-1,2,5-thiadiazole-3,4-diamine 1-oxide.

Selective H-2 antagonists include the 2-guanidino-4-heteroarylthiazoles meeting the above criteria which are disclosed in U.S. Pat. No. 4,374,843 issued to LaMattina and Lipinski on Feb. 22, 1983. Preferred is zaltidine (CP-57361-01), (4-(2-methyl-1H-imidazol-4-yl)-2-thiazolyl)-guanidine.

Selective H-2 antagonists include the N-alkyl-N'-((2-(aminoalkyl)-4-thiazolylmethyl)thioalkyl)guanidines, thioureas, ethenediamines and related compounds meeting the above criteria which are disclosed in U.S. Pat. No. 4,375,547 issued to Ploch on Mar. 1, 1983. Preferred is nizatidine (LY-139037, ZL-101), N-(2-(((2-((dimethylamino)methyl)-4-thiazolyl) methyl)thio)ethyl)-N'-methyl-2-nitro-1,1-ethenediamine: Nizatidine is also disclosed in the Merck Index, 11th edition (1989), p. 1052 (entry no. 6582), and Physicians' Desk Reference, 46th edition (1992), p. 1246.

Selective H-2 antagonists include the imidazolylphenyl amidines meeting the above criteria which are disclosed in U.S. Pat. No. 4,386,099 issued to Cereda, Donetti, Soldato and Bergamaschi on May 31, 1983. Preferred is mifentidine (DA-4577), N-(4-(1H-imidazol-4-yl)phenyl)-N'-(1-methylethyl)methanimidamide. Mifentidine and its dihydrochloride salt are disclosed in the Merck Index, 11th edition (1989), p. 973 (entry no. 6108).

Selective H-2 antagonists include the 1-(substituted amino)-2-(amino or substituted amino)cyclobutene-3,4-diones meeting the above criteria which are disclosed in U.S. Pat. No. 4,390,701 issued to Algieri and Crenshaw on Jun. 28, 1983. Preferred are BMY-25368 (SKF-94482), 3-amino-4-((3-(3-(1-piperidinylmethyl)phenoxy)propyl)amino)-3-cyclobutene-1,2-dione and its hydrochloride salt.

Selective H-2 antagonists include the 3-(hydroxy or amino)-4-(substituted amino)- and 3,4-di(substituted amino)-1,2,5-thiadiazole 1-oxides and 1,1-dioxides meeting the above criteria which are disclosed in U.S. Pat. No. 4,394, 508 issued to Crenshaw and Algiere on Jul. 19, 1983. Preferred is BL-6341A (BMY-26539), (4-(((2-((4-amino-1,2,5-thiadiazol-3-yl)amino)ethyl)thio)methyl)-2-thiazolyl)-guanidine, S-oxide.

Selective H-2 antagonists include the cycloalkylamino derivatives meeting the above criteria which are disclosed in U.S. Pat. No. 4,427,685 issued to Stemp on Jan. 24, 1984. Preferred is N-(2-(((5-dimethylaminomethyl-2-furanyl)methyl)thio)ethyl)-N'-cyclo-octyl-2-nitro-1,1'-ethenediamine.

Selective H-2 antagonists include alcohol guanidine derivatives meeting the above criteria which are disclosed in U.S. Pat. No. 4,451,463 issued to Large on May 29, 1984. Preferred is ICI-162846, 3-((imino((2,2,2-trifluoroethyl) amino)methyl)amino)-1H-pyrazole-1-pentanamide.

Selective H-2 antagonists include the thioalkylamide of nicotinic acid 1-oxide compounds meeting the above criteria which are disclosed in U.S. Pat. No. 4,474,790 issued to Nisato and Boveri on Oct.2, 1984. Preferred is ramixotidine (CM-57755), N-(2-(((5-((dimethylamino)methyl)-2-furanyl)methyl)thio)ethyl)-3-pyridinecarboxamide 1-oxide.

Selective H-2 antagonists include the benzo-fused heterocyclic compounds meeting the above criteria which are disclosed in U.S. Pat. No. 4,490,527 issued to Schiehser and Strike on Dec. 25, 1984. Preferred is Wy-45727, N-(2-(((5-dimethylamino)methyl)-2-furanyl)methyl)thio)ethyl)thieno (3,4-d)isothiazol-3-amine 1,1-dioxide.

Selective H-2 antagonists include the N-substituted nicotinamide 1-oxide compounds meeting the above criteria which are disclosed in U.S. Pat. No. 4,514,408 issued to Nisato and Boveri on Apr. 30, 1985. Preferred is SR-58042, (N-(3-(3-(3-methyl)piperidinomethyl)phenoxy)propyl)-3-pyridinecarboxamide 1-oxide.

Selective H-2 antagonists include the 3-(amino or substituted amino)-4-(substituted amino)-1,2,5-thiadiazoles meeting the above criteria which are disclosed in U.S. Pat. Nos. 4,528,377 and 4,600,779 issued to Crenshaw and Algieri on Jul. 9, 1985 and Jul. 15, 1986, respectively. Preferred is BMY-25405, N-(3-(3-(1-piperidinylmethyl)phenoxy)propyl)-1,2, 5-thiadiazole-3,4-diamine monohydrochloride.

Selective H-2 antagonists include the triazole amine derivatives meeting the above criteria which are disclosed in U.S. Pat. No. 4,536,508 issued to Clitherow, Price, Bradshaw, Martin-Smith, Mackinnon, Judd and Hayes on Aug. 20, 1985. Preferred is loxtidine (AH-23844), 1-methyl-5-((3-(3-(1-piperidinylmethyl)phenoxy)propyl)amino)-1H-1,2,4-triazole-3-ethanol.

Selective H-2 antagonists include the guanidino-heterocyclyl-phenylamidines meeting the above criteria which are disclosed in U.S. Pat. Nos. 4,548,944 and 4,645,841 issued to Bietti, Cereda, Donetti, Soldato, Giachetti and Micheletti on Oct. 22, 1985, and Feb. 24, 1987, respectively. Preferred is DA-4634, (4-(3-(((methylamino)methylene)amino)phenyl)-2-thiazolyl)-guanidine.

Selective H-2 antagonists include the amidine derivatives of 2-substituted 4-phenylimidazole compounds meeting the above criteria which are disclosed in U.S. Pat. No. 4,649,150 issued to Bietti, Cereda, Donetti, Giachetti and Pagani on Mar. 10, 1987. Preferred is bisfentidine (DA-5047), N-(1-methylethyl)-N'-(4-(2-methyl-1H-imidazol-4-yl)phenyl)-ethanimidamide.

Selective H-2 antagonists include the triazole amine compounds meeting the above criteria which are disclosed in U.S. Pat. No. 4,670,448 issued to Clitherow, Bradshaw, MacKinnon, Judd, Bays, Hayes and Pearce on Jun. 2, 1987. Preferred is sufotidine (AH-25352), 1-methyl-3-((methylsulfonyl)methyl)-N-(3-(3-(1-piperidinylmethyl)phenoxy)propyl)-1H-1, 2,4-triazol-5-amine.

Selective H-2 antagonists include the sulfonamidines meeting the above criteria which are disclosed in U.S. Pat. No. 4,728,755 issued to Foguet, Anglada, Costello, Sacristan and Ortiz on Mar. 1, 1988. Preferred is ebrotidine (FI-3542), N-(((2-(((2-((aminoiminomethyl)amino)-4-thiazolyl)methyl)thio)ethyl)amino)methylene)-4-bromo-benzene-sulfonamide.

Selective H-2 antagonists include the 1,3,4-thiadiazole derivatives meeting the above criteria which are disclosed in U.S. Pat. No. 4,738,960 issued to Schickaneder; Heter, Wegner, Schunack, Szelenyi, Postius and Ahrens on Apr. 19, 1988. Preferred is HE-30-256, 1-(3-(3-(piperidinomethyl)phenoxy)propylamino)-5-pyridin-2-sulfenamido-1,3,4-thiadiazole.

Selective H-2 antagonists include the ethylenediamine and guanidine-derivatives meeting the above criteria which are disclosed in U.S. Pat. No. 4,738,983 issued to Emig, Scheffler, Thiemer and Weischer on Apr. 19, 1988. Preferred is D-16637, N-(2(((5-((tricyclo(2.2.1.0)hept-3-ylamino)methyl-2-furanyl)methyl)thio)ethyl)-N-methyl-2-nitro-1,1-ethenediamine HCl.

Selective H-2 antagonists include the 4-aminomethyl-pyridyl-2-oxy derivatives meeting the above criteria which are disclosed in U.S. Pat. Nos. 4,912,101 and 4,977,267 issued to Hirakawa, Kashiwaba, Matsumoto, Hosoda, Sekine, Isowa, Yamaura, Sekineland Nishikawa on Mar. 27 and Dec. 11, 1990, respectively. Preferred is FRG-8813, N-(4-(4-(piperidinomethyl)pyridyl-2-oxy)-(Z)-2-butenyl)-2-(furfurylsulfinyl)acetamide.

Selective H-2 antagonists include the alkylamide derivatives meeting the above criteria which are disclosed in U.S. Pat. No. 4,837,316, issued to Sekine, Hirakawa, Kashiwaba, Yamaura, Harada, Katsuma, Matsumoto, Sekine and Isowa on Jun. 6, 1989. Preferred is FRG-8701, N-(3-(3-(piperidinomethyl)phenoxy)propyl)-2-(furfurylsulfinyl)acetamide.

Selective H-2 antagonists include the N,N'-disubstituted guanidine compounds meeting the above criteria which are disclosed in U.K. Patent Specification No. 1,531,237 of Durant, Ganellin and Parsons published on Nov. 8, 1978. Preferred is impromidine.

Selective H-2 antagonists include the 3,4-diamino-1,2,5-thiadiazole compounds meeting the above criteria which are disclosed in European Patent Application No. 0,040,696 of Baldwin, Bolhofer, Lumma, Amato, Karady and Weinstock, published Dec. 2, 1981. Preferred is L-643728, 4-amino-3-(2-(5-(dimethylaminomethyl)-2-furanylmethylthio)ethylamino)-5-ethoxycarbonyl-isothiazole-1,1-dioxide.

Selective H-2 antagonists include the 2-substituted amino-4(1H)-pyrimidone derivatives meeting the above criteria which are disclosed in European Patent Application No. 0,186,275 of Yanagisawa, Ohta, Takagi and Takeuchi, published Jul. 2, 1986. Preferred is HB-408, 5-butyl-6-methyl-2-(3-(3-(piperidinomethyl)phenoxy)propylamino)pyrimidin-4(1 H)-one.

Selective H-2 antagonists include the active compounds meeting the above criteria which are disclosed in Hoffman, J. M., A. M. Pietruszkiewicz, C. N. Habecker, B. T. Phillips, W. A. Bolhofer, E. J. Cragoe, M. L. Torchiana, W. C. Lumma and J. J. Baldwin, "Conformational Requirements for Histamine H2-Receptor Inhibitors: A Structure-Activity Study of Phenylene Analogues Related to Cimetidine and Tiotidine", J. Med. Chem., Vol. 26 (1983), p. 140-144. Preferred is L-643441, N-(3-(3-(1-piperidinylmethyl)phenoxy)propyl)-1,2,5-thiadiazole-3,4-diamine 1-oxide.

Selective H-2 antagonists include the active compounds meeting the above criteria which are disclosed in Borchers, V. A., H. Engler, I. Szelenyi and W. Schunack, "Synthese und H2-antihistaminische Wirkung N,N'-bismidazo(substituierter Thioharnstoffe, Cyanoguanidine und 2-Nitro-1,1-ethendiamine", Arzneim. Forsch., Vol. 32 (1982), pp. 1509-1512. Preferred is N-cyano-N',N"-bis(2-((5-methyl-4-imidazolyl)methylthio)ethyl)guanidine.

Selective H-2 antagonists include the active compounds meeting the above criteria which are disclosed in Elz, V. S. and W. Schunak, "H2-antagonistische Aktivitat Impromidinanaloger Cyanoguanidine", Arzneim.-Forsch., Vol. 38(I), No. 1 (1988), pp. 7-10. Preferred is N-cyano-N'-(2-(4,5,6,7-tetrahydrobenzimidazol-2-yl)ethyl)-1-N"-(2-((5-methylimidazol-4-yl)methyl thio)ethyl)guanidine.

Selective H-2 antagonists include the active compounds meeting the above criteria which are disclosed in Borella, L., J. Russell, T. J. Rimele, D. Grimes, A. Failli and G. N. Mir, "Antisecretory and Antiulcer Activities of a Potent New Histamine H2-Receptor Antagonist with an Intermediate Duration of Action", Arzneim. Forsch., Vol. 38(I), No. 3 (1988), pp. 366-372. Preferred is AY-29315, 4-(dimethylamino)-N-(2-((4-((3-(3-(1-piperidinylmethyl)phenoxy)propyl)amino)-1,2,5-thiadiazol-3-yl)amino)ethyl)butanamide S-oxide.

Selective H-2 antagonists include the active compounds meeting the above criteria which are disclosed in Muramatsu, M., Y. Isobe, I. Arai, H. Hirose-Kijima, C. Usuki-Ito, H. Nagai, H. Aihara and S. Otomo, "Effects of the New H2-Receptor Antagonist 3-Amino-4-(4-(4-(1-piperidinomethyl)-2-Pyridyloxy)-cis-2-butenylamino)-3-cyclobutene-1,2-dione Hydrochloride on Gastric Acid Secretion and Ulceration", Arzneim. Forsch., Vol. 40(I), No. 1 (1990), pp. 49-54. Preferred is IT-066, 3-imino-4-(4-(4-(1-piperidinomethyl)-2-pyridoxy)-cis-2-butenylamino)-3-cyclobutene-1,2-dione HCl.

Selective H-2 antagonists include the active compounds meeting the above criteria which are disclosed in Katz, L. B., A. J. Tobia and D. A. Shriver, "Effects of ORF-17583, Other Histamine H2-Receptor Antagonists and Omeprazole on Gastric Acid Secretory States in Rats and Dogs", The Journal of Pharmacology and Experimental Therapeutics, Vol. 242 (1987), pp. 437-442. Preferred is ORF-17583 (BL-6217), N-(2-(((5-((dimethylamino)methyl)-2-furanyl)methyl)thio)ethyl)-N'-methyl-1,2,5-thiadiazole-3,4-diamine 1-oxide.

Selective H-2 antagonists include the active compounds meeting the above criteria which are disclosed in Nielsen, S. T., P. Dove, G. Palumbo, A. Sandor, C. Buonato, G. Schiehser, A. Santilli and D. Strike, "Two H2-Receptor Antagonists as Inhibitors of Gastric Acid Secretion", Fed. Proc., Vol. 43 (1984), Abst. No. 4617. Preferred are Wy-45086, N-(3-(3-((1-piperidinyl)methyl)phenoxy)propyl)-3-benzisothiazoleamine 1,1-dioxide and Wy-45253, N-(3-(3-(1-pyrrolidinylmethyl)phenoxy)propyl)-1,2-benzisothiazol-3-amine 1,1-dioxide HCl.

Selective H-2 antagonists include the active compound meeting the above criteria which are disclosed in Goto, Y., M. Yamada and T. Nagata, "Antisecretory Activity of a Novel H-2 Antagonist, IK-82029, Is Specific to Histamine-2 Receptors in the Rat", Gastroenterology, Vol. 90 (1986), p. 1435, IK-82029.

Selective H-2 antagonists include the active compounds meeting the above criteria which are disclosed in Tsuriya, Y., H. Matsukawa, H. Aoky and M. Seye, "The Pharmacological Properties of 2-N-(3-(3-(1-piperidinomethyl)-phenoxy)propyl)amino-5-amino-1,3,4-thiadiazole (TAS), a New Histamine H2—Receptor Antagonist: Comparison with Ranitidine and Cimetidine", Japan J. Pharmacol., Vol. 63 (Suppl.) (1984), p. 90P-91P. Preferred is TAS, N,N-(3-(1-piperidinomethyl)phenoxypropyl)amino-5-amino-1,3,4-thiadiazole.

Selective H-2 antagonists include the active compounds meeting the above criteria which are disclosed in Oshita, M., K. Morikawa, T. Aratani, H. Kato and Y. Ito, "Pharmacological Studies of 2-(3-(3-(1-Piperidinylmethyl)phenoxy)propylamino)-4(3H)-Quinazolinone (NO-794), a New Histamine H2-Receptor Antagonist", Japan J. Pharmacol., Vol. 42 (1986), pp. 229-235. Preferred is NO-794, 2-((3-(3-(1-piperidinylmethyl)phenoxy)propyl)amino-4(3H)-quinazolinone.

Selective H-2 antagonists include the active compounds meeting the above criteria which are disclosed in Nishida, A., K. Miyata, I. Yanagisawa, M. Takeda, T. Kamato, H. Ito, H.

Yuki, M. Yamano, R. Tsutsumi and K. Honda, "Effects of YM-14471, a Potent and Long-Lasting Histamine H2-Receptor Antagonist, on Gastric Acid Secretion in Rats and Dogs", Japan J. Pharmacol., Vol. 55 (Suppl 1) (1991), Abstract P497). Preferred is YM-14471, 2-(2-(2-diaminomethyleneamino) thiazol-4-ylmethylthio)ethyl)-5-(3-(diethylamino)propyl)-6-methyl-pyrimidin-4(1H)-one 3 HCl.

Selective H-2 antagonists include the active compounds meeting the above criteria which are disclosed in Ueda, I., K. Ishii, K. Shinozaki, M. Seiki, H. Arai and M. Hatanaka, "Synthesis and Pharmacological Properties of N-[3-{3-(1-Piperidinylmethyl)phenoxy)propyl]-2-(2-hydroxy-ethylthio)acetamide and Related Compounds as Antiulcer Agents. I", Chem. Pharm. Bull., Vol. 38(11) (1990), p. 3035-3041. Preferred is N-(3-(3-(1-piperidinylmethyl)phenoxy) propyl)-2-(2-hydroxyethylthio)acetamide.

Selective H-2 antagonists include the active compounds meeting the above criteria which are disclosed in Dialog File 3128, Pharmaprojects Database entry no. 00015689, Mar. 21, 1991, PJB Publications Ltd., Richmond, Surrey, UK. Preferred is Z-300.

Selective H-2 antagonists include the active compound meeting the above criteria which is disclosed in Nelson, S. T., "H2-receptor Antagonist and Gastric Acid Antisecretory Properties of Wy-45,662", Agents and Actions, Vol. 19(3/4) (1986), pp. 158-163: Wy-45662, N-(3-(3-(1-piperidinylmethyl)phenoxy)propyl)-thieno(3,4-d)isothiazol-3-amine 1,1-dioxide.

Selective H-2 antagonists include the active compounds meeting the above criteria which are disclosed in Michael, J. D., J. D. Coombes, S. J. Cousins, D. B. Norris, T. J. Rising, B. C. Ross and A. Steward, "Synthesis of 4-Alkyl-1,2,4,6-thiatriazine 1,1-dioxide derivatives: Potent New Histamine H-2 Antagonists", 190th ACS (Chicago), 1985, MEDI 33. Preferred is tuvatidine (HUK-978), (4-(((2-((5-amino-4-methyl-4H-1,2,4,6-thiatriazin-3-yl)amino)ethyl)thio)methyl)-2-thiazolyl)guanidine S,S-dioxide.

Selective H-2 antagonists include N-(3-(3-(1-piperidinyl) phenoxy)propyl)thieno(3,4-d)-isothiazol-3-amine-1,1-dioxide, meeting the above criteria, as disclosed in Santilli, A. A., A. C. Scotese, R. L. Morris, G. A. Schiehser, D. M. Teller, S. T. Nielsen and D. P. Strike, "Syntheses and Gastric Acid Antisecretory Properties of the H2-Receptor Antagonist N-[3-[3-(1-Piperidinylmethyl)phenoxy]propyl]thieno[3,4-d]isothiazol-3-amine 1,1-Dioxide and Related Derivatives", J. Med. Chem., Vol. 31 (1988), pp. 1479-1486.

Selective H-2 antagonists include FCE-23067, 2-guanidine-5-(N-isopropylcarbamoyl)-4,5,6,7-tetrahydrothiazole (5,4-c)pyridine, meeting the above criteria.

Selective H-2 antagonists include CRC-1970, N-cyano-N'-methyl-N"-(2(((2-(((4-methyl-5-oxazolyl)methyl)thio) ethyl)-guanidine, meeting the above criteria.

Selective H-2 antagonists include RGW-2568 (WHR-2568), N5-(3-((2,3-dihydro-1-(1-piperidinyl)-1H-inden-4-yl)oxy)propyl)-methyl-1H-1,2,4-triazole-3,5-diamine, meeting the above criteria.

Selective H-2 antagonists include the following compounds meeting the above criteria: 5,6-substituted 4-pyrimidone compounds disclosed in Spengler, J.-P., K. Wegner and W. Schunack, "H2-Antihistaminics. 20. Structure-Activity Relationships in H2-Receptor Antagonists Containing a 4-Pyrimidone Moiety", Agents and Actions, Vol. 14, No. 3/4 (1984), pp. 566-568; 3- and 2-indole derivatives disclosed in Tecle, H., L. Robichaud, and C. F. Schwender, "Potential Histamine H2-Receptor Blockers. 3- and 2-indole Derivatives as Immobile Analogues of Tautomeric Forms of Cimetidine", J. Med. Chem., Vol. 24 (1981), pp. 1095-1097; benzylhistamine compounds disclosed in Emmett, J. C., G. J. Durant, C. R. Ganellin, A. M. Roe and J. L. Turner, "Potential Histamine H2-Receptor Antagonists. 4. Benzylhistamines", J. Med. Chem., Vol. 25 (1982), pp. 1168-1174; (imidazolylphenyl)guanidine, imidazolylbenzamidine, and (imidazolylphenyl)formamidine compounds disclosed in Donetti, A., E. Cereda, E. Bellora, A. Gailazzi, C. Bazzano, P. Vanoni, P. Del Soldato, R. Micheletti, F. Pagani and A. Giachetti, "(Imidazolylphenyl)formamidines. A Structurally Novel Class Of Potent Histamine H2 Receptor Antagonists", J. Med. Chem., Vol. 27 (1984), pp. 380-386; N-cyano and N-carbamoyl amidine derivatives disclosed in Yanagisawa, I., Y. Hirata and Y. Ishii, "Histamine H2 Receptor Antagonists. 1. Synthesis of N-Cyano and N-Carbamoyl Amidine Derivatives and Their Biological Activities", J. Med. Chem. Vol. 27 (1984), pp. 849-857; biaryl pyridyl compounds disclosed in Lipinski, C. A., J. L. LaMattina and L. A. Hohnke, "Pseudosymmetry and Bioisosterism in Biaryl Pyridyl Competitive Histamine H2-Receptor Antagonists", J. Med. Chem., Vol. 28 (1985), pp. 1628-1636; cimetidine analogs disclosed in Young, R. C., G. J. Durant, J. C. Emmett, C. R. Ganellin, M. J. Graham, R. C. Mitchell, H. D. Prain and M. L. Roantree, "Dipole Moment in Relation to H2 Receptor Histamine Antagonist Activity for Cimetidine Analogues", J. Med. Chem., Vol. 29 (1986), pp. 44-49; biaryl imidazolyl and triazolyl compounds disclosed in Lipinski, C. A., J. L. LaMattina P. J. Oates, "Bioisosteric Prototype Design of Biaryl Imidazolyl and Triazolyl Competitive Histamine H2-Receptor Antagonists", J. Med. Chem., Vol. 29 (1986), pp. 2154-2163; zwitterionic analogues of cimetidine disclosed in Young, R. C., C. R. Ganellin, M. J. Graham, R. C. Mitchell, M. L. Roantree and Z. Tashma, "Zwitterionic Analogues of Cimetidine as H2 Receptor Antagonists", J. Med. Chem., Vol. 30 (1987), pp. 1150-1156; N-substituted thieno(3,4-d) isothiazol-3-amine 1,1-dioxides and analogs disclosed in Santilli, A. A., A. C. Scotese, R. L. Morris, G. A. Schiehser, D. M. Teller, S. T. Nielsen and D. P. Strike, "Syntheses and Gastric Acid Antisecretory Properties of the H2-Receptor Antagonist N-(3-(3-(1-Piperidinylmethyl)phenoxy)propyl)thieno(3,4-d)isothiazol-3-amine 1,1-Dioxide and Related Derivatives", J. Med. Chem., Vol. 31 (1988), pp. 1479-1486; pyrimidine and reduced pyrimigine analogues disclosed in El-Badry, O. M. and E. E. Knaus, "Pyridine and Reduced Pyridine Analogues as Histamine H2-Receptor Antagonists", Eur. J. Med.—Chem. Chim. Ther., Vol. 20, No. 5 (1985), pp. 403-407; pyrimidine and reduced pyrimidine analogues of "Pyridine Analogues of Ranitidine as Histamine H2-Receptor Antagonists", Eur. J. Med. Chem.—Chim. Ther., Vol. 20, No. 5 (1985), pp. 409-413; diaminofurazan compounds disclosed in Sorba, G., R. Calvino, A. Defilippi, A. Gasco and M. Orsetti, "Potential Histamine H2-Receptor Antagonists: Diaminofurazan, a New Urea Equivalent Group", Eur. J. Med. Chem.—Chim. Ther., Vol. 20, No. 6 (1985), pp. 571-574; ranitidine analogues containing 5(6)substituted benzimidazole moieties disclosed in Sorba, G., A. Garrone, A. Serafino, A. Gasco and M. Orsetti, "Potential Histamine H2-Receptor Antagonists: Ranitidine Analogues Containing 2-Amino-5(6)-Substituted-Benzimidazole Moieties", Eur. J. Med. Chem.—Chim. Ther., Vol. 21, No. 5 (1986), pp. 391-395; cimetidine and impromidine congeners disclosed in Sterk, G. J., H. Van Der Goot H. Timmerman, "Studies on Histaminergic Compounds VI. Synthesis and Structure—Activity Relationships of a Series of Cimetidine and impromidine Congeners", Eur. J. Med. Chem., Vol. 22 (1987), pp. 427-432; pyridine and reduced pyridine analogues of cimetidine disclosed in El-Badry, O. M., E. E. Knaus and J. H. McNeill, "Pyridine and Reduced Pyridine Analogues of Cimetidine as Histamine H2-Receptor Antagonists", Euro. J. Med. Chem., Vol. 22 (1987), pp. 579-582; N'-substituted thiourea, cyanoguanidine and dithiooxamide compounds disclosed in Barzen, R. and W. Schunack, "Synthese und H2-Antihistaminische Wirkung N,N'-Substituierter Thioharnstoffe, Cyanoguanidine und Dithiooxamide", Arch. Pharm. (Weinheim), Vol. 314 (1981), pp. 617-622; ketene N,N-acetal compounds disclosed in Barzen, R. and W. Schunack, "Keten-N,N-Acetale Mit H2-Antihistaminischer Wirkung", Vol. 315 (1982), pp. 680-684; guanidinothiazole compounds disclosed in Trumm, V. K.-A. and W. Schunack, "Guanidinothiazole Mit H2-Antihistaminischer Wirkung", Arzneim.-Forsch./Drug Res., Vol. 33(1), No. 2 (1983), pp. 188-190, and Spengier, V. J.-P and W. Schunack, "Razemische Guanidinothiazole Mit H2-Antihistaminischer Wirkung", Arzneim-Forsch./Drug Res., Vol. 33(1), No. 3 (1983), pp. 377-380; N,N'-bisheteroaryl substituted cyanoguanidine and 2-nitro-1,1-ethenediamine compounds disclosed in Borchers, V. A., S. Postius, I. Szelenyi and W. Schunack, "Synthese und H2-Antihistaminische Wirkung N,N'-Bisheteroaryl-Substituierter Cyanoguanidine und 2-Nitro-1,1-Ethendiamine", Arzneim.-Forsch./Drug Res., Vol. 34(II), No. 7 (1984), pp. 751-754.

All of the above patents and other references which disclose H-2 antagonists and methods of testing H-2 and H-1 antagonists are hereby incorporated herein by reference.

If present, the H-2 antagonist agents generally comprise from about 0.001% to about 20%, more preferably from about 0.01% to about 15%, more preferably still from about 0.1% to about 10%, still more preferably from about 1% to about 5%, by weight of the compositions of the present invention. In addition to cimetidine, preferred H-2 antagonists include ranitidine, famotidine, roxatidine, nizatidine and mifentidine.

Anti-inflammatory Agents

Anti-inflammatory agents may also be present in the oral compositions of the present invention. Such agents may include, but are not limited to, lipoxygenase inhibitors, such as nordihydroguaiaretic acid; cyclo-oxygenase inhibitors such as flurbiprofen and triclosan; and non-steroidal anti-inflammatory agents such as aspirin, ketorolac, flurbiprofen, ibuprofen, naproxen, indomethacin, aspirin, ketoprofen, piroxicam and meclofenamic acid, rofecoxib, celecoxib, and mixtures thereof. If present, the anti-inflammatory agents generally comprise from about 0.001% to about 5% by weight of the compositions of the present invention. Ketorolac is described in U.S. Pat. No. RE 036,419, issued Nov. 30, 1999; U.S. Pat. No. 5,785,951, issued Jul. 28, 1998 and U.S. Pat. No. 5,464,609, issued Nov. 7, 1995, all incorporated herein by reference in their entirety.

Metalloproteinase Inhibitors

Metalloproteinase inhibitors may also be present in the oral compositions of the present invention. Metalloproteinases (MPs) are enzymes that often act on the intercellular matrix, and thus are involved in tissue breakdown and remodeling. Examples of MPs include human skin fibroblast collagenase, human skin fibroblast gelatinase, human sputum collagenase, aggrecanase and gelatinase, and human stromelysin. Collagenase, stromelysin, aggrecanase and related enzymes are thought to be important in mediating the symptomatology of a number of diseases including periodontal disease. Potential therapeutic indications of MP inhibitors have been discussed in the literature, including treatment of: rheumatoid arthritis (Mullins, D. E., et al., Biochim. Biophys. Acta. (1983) 695: 117-214); osteoarthritis (Henderson, B., et al., Drugs of the Future (1990) 15:495-508); the metastasis of tumor cells (ibid, Broadhurst, M. J., et al., European Patent Application 276,436 (published 1987), Reich, R., et al., 48 Cancer Res. 3307-3312 (1988); and various ulcerations or ulcerative conditions of tissue. For example, ulcerative conditions can result in the cornea as the result of alkali burns or as a result of infection by *Pseudomonas aeruginosa, Acanthamoeba*, Herpes simplex and vaccinia viruses. Other examples of conditions characterized by undesired metalloprotease activity include periodontal disease, epidermolysis bullosa, fever, inflammation and scleritis (DeCicco, et al., WO 95/29892 published Nov. 9, 1995).

Metalloproteinase inhibitors useful for the present compositions may include, but are not limited to, hydroxamic acid derivatives, phosphinic acid amides, and heteroatom-containing cyclic and acyclic structures such as disclosed in U.S. Pat. No. 6,015,912, issued Jan. 18, 2000; U.S. Pat. No. 5,830,915, issued Nov. 3, 1998; U.S. Pat. No. 5,672,598, issued Sep. 30, 1997 and U.S. Pat. No. 5,639,746, issued Jun. 17, 1997 and in WO 99/52868; WO 99/06340; WO 98/08827; WO98/08825; WO 98/08823; WO 98/08822; WO 98/08815; and WO 98/08814, all assigned to the Procter & Gamble Company and incorporated herein by reference in their entirety.

If present, the metalloproteinase inhibitors generally comprise at least about 0.001% by weight of the compositions of the present invention.

Other Host-Response Modulating Agents

Modifiers of cell redox status include anti-oxidants such as N-acetyl cysteine and gallic acid; anti-oxidant enzyme inducers such as anethole-dithiothione, oltipraz, PDTC and indole-3-carbinol; polyphenols such as epi-gallo catechin gallate and curcumin; and nutrients and vitamins such as Co-enzyme Q10, pyrroloquinoline quinone (PQQ), vitamins C, E, and A, folate, combinations of C and E, and zinc salts.

Inhibitors of activation of NF-kB include caffeic acid phenethyl ester and preparations of bee propolis.

Additional Therapeutic Agents

It is recognized that in certain forms of therapy, combinations of therapeutic agents in the same delivery system may be useful in order to obtain an optimal effect. Thus, for example, the present compositions may comprise an additional agent such as antimicrobial/antiplaque agents, biofilm inhibiting agents, antibiotics; analgesics and local anesthetic agents; dentinal desensitizing agents; and odor masking agents. The host-response modulating agent may be combined with one or more of such agents in a single delivery system to provide combined effectiveness.

Antimicrobial antiplaque agents may include, but are not limited to, chlorite ion agent; triclosan, 5-chloro-2-(2,4-dichlorophenoxy)-phenol, as described in The Merck Index, 11th ed. (1989), pp. 1529 (entry no. 9573) in U.S. Pat. No. 3,506,720, and in European Patent Application No. 0,251,591 of Beecham Group, PLC, published Jan. 7, 1988; chlorhexidine (Merck Index, no. 2090), alexidine (Merck Index, no. 222); hexetidine (Merck Index, no. 4624); sanguinarine (Merck Index, no. 8320); benzalkonium chloride (Merck Index, no. 1066); salicylanilide (Merck Index, no. 8299); domiphen bromide (Merck Index, no. 3411); cetylpyridinium chloride (CPC) (Merck Index, no. 2024; tetradecylpyridinium chloride (TPC); N-tetradecyl-4-ethylpyridinium chloride (TDEPC); octenidine; delmopinol, octapinol, and other piperidino derivatives; nisin preparations; zinc ion agents; stannous ion agents; essential oils (including thymol, methyl salicylate, eucalyptol, menthol) and analogs and salts of the above antimicrobial antiplaque agents. If present, the antimicrobial antiplaque agents generally comprise at least about 0.01% by weight of the compositions of the present invention.

Biofilm inhibiting agents prevent bacterial adherence, colonization in the mouth or maturation into biofilms, which are defined as bacterial populations adherent to each other and/or to surfaces or interfaces. These agents are thus effective in controlling bacterial populations that mediate periodontal disease and other oral cavity infections. Examples of biofilm inhibiting agents are furanones, cell wall lytic enzymes such as lysozyme, plaque matrix inhibitors such as dextranases and mutanases, and peptides such as bacteriocins, histatins, defensins and cecropins.

Other optional therapeutic agents include antibiotics such as augmentin, amoxicillin, tetracycline, doxycycline, minocycline, metronidazole, neomycin, kanamycin, or clindamycin; dentinal desensitizing agents such as strontium chloride, potassium nitrate, stannous fluoride or sodium fluoride; odor masking agents such as peppermint oil or chlorophyll; local anesthetic agents such as lidocaine or benzocaine; nutritional agents such as amino acids, essential fats, and minerals; and peroxides such as urea peroxide.

Pharmaceutically-Acceptable Carrier

By "pharmaceutically-acceptable carrier", as used herein, is meant a suitable vehicle including one or more compatible solid or liquid filler diluents, excipients or encapsulating substances which are suitable for topical, oral administration. By "compatible," as used herein, is meant that the components of the composition are capable of being commingled without interaction in a manner which would substantially reduce the composition's stability and/or efficacy, according to the compositions and methods of the present invention.

The carriers of the present invention can include the usual and conventional components of toothpastes (including gels and gels for subgingival application), mouth rinses, mouth sprays, dental solutions including irrigation fluids, chewing gums, and lozenges (including breath mints) as more fully described hereinafter.

The choice of a carrier to be used is basically determined by the way the composition is to be introduced into the oral cavity. If a toothpaste (including tooth gels, etc.) is to be used, then a "toothpaste carrier" is chosen as disclosed in, e.g., U.S. Pat. No. 3,988,433, to Benedict, the disclosure of which is incorporated herein by reference (e.g., abrasive materials, sudsing agents, binders, humectants, flavoring and sweetening agents, etc.). If a mouth rinse is to be used, then a "mouth rinse carrier" is chosen, as disclosed in, e.g., U.S. Pat. No. 3,988,433 to Benedict (e.g., water, flavoring and sweetening agents, etc.). Similarly, if a mouth spray is to be used, then a "mouth spray carrier" is chosen or if a lozenge is to be used, then a "lozenge carrier" is chosen (e.g., a candy base), candy bases being disclosed in, e.g., U.S. Pat. No. 4,083,955, to Grabenstetter et al., which is incorporated herein by reference; if a chewing gum is to be used, then a "chewing gum carrier" is chosen, as disclosed in, e.g., U.S. Pat. No. 4,083,955, to Grabenstetter et al., which is incorporated herein by reference (e.g., gum base, flavoring and sweetening agents). If a sachet is to be used, then a "sachet carrier" is chosen (e.g., sachet bag, flavoring and sweetening agents). If a subgingival gel is to be used (for delivery of actives into the periodontal pockets or around the periodontal pockets), then a "subgingival gel carrier" is chosen as disclosed in, e.g. U.S. Pat. No. 5,198,220, Damani, issued Mar. 30, 1993, P&G, U.S. Pat. No. 5,242,910, Damani, issued Sep. 7, 1993, P&G, all of which are incorporated herein by reference. Carriers suitable for the preparation of compositions of the present invention are well known in the art. Their selection will depend on secondary considerations like taste, cost, and shelf stability, etc.

Preferred compositions of the subject invention are in the form of dentifrices, such as toothpastes, tooth gels and tooth powders. Components of such toothpaste and tooth gels generally include one or more of a dental abrasive (from about 10% to about 50%), a surfactant (from about 0.5% to about 10%), a thickening agent (from about 0.1% to about 5%), a humectant (from about 10% to about 55%), a flavoring agent (from about 0.04% to about 2%), a sweetening agent (from about 0.1% to about 3%), a coloring agent (from about 0.01% to about 0.5%) and water (from about 2% to about 45%). Such toothpaste or tooth gel may also include one or more of an anticaries agent (from about 0.05% to about 0.3% as fluoride ion), and an anticalculus agent (from about 0.1% to about 13%). Tooth powders, of course, contain substantially all non-liquid components.

Other preferred compositions of the present invention are non-abrasive gels, including subgingival gels, which generally include a thickening agent (from about 0.1% to about 20%), a humectant (from about 10% to about 55%), a flavoring agent (from about 0.04% to about 2%), a sweetening agent (from about 0.1% to about 3%), a coloring agent (from about 0.01% to about 0.5%), and the balance water. The compositions may comprise an anticaries agent (from about 0.05% to about 0.3% as fluoride ion), and an anticalculus agent (from about 0.1% to about 13%).

Other preferred compositions of the subject invention are mouthwashes, including mouth sprays. Components of such mouthwashes and mouth sprays typically include one or more of water (from about 45% to about 95%), ethanol (from about 0% to about 25%), a humectant (from about 0% to about 50%), a surfactant (from about 0.01% to about 7%), a flavoring agent (from about 0.04% to about 2%), a sweetening agent (from about 0.1% to about 3%), and a coloring agent (from about 0.001% to about 0.5%). Such mouthwashes and mouth sprays may also include one or more of an anticaries agent (from about 0.05% to about 0.3% as fluoride ion), and an anticalculus agent (from about 0.1% to about 3%).

Other preferred compositions of the subject invention are dental solutions including irrigation fluids. Components of such dental solutions generally include one or more of water (from about 90% to about 99%), preservative (from about 0.01% to about 0.5%), thickening agent (from 0% to about 5%), flavoring agent (from about 0.04% to about 2%), sweetening agent (from about 0.1% to about 3%), and surfactant (from 0% to about 5%).

Chewing gum compositions typically include one or more of a gum base (from about 50% to about 99%), a flavoring agent (from about 0.4% to about 2%) and a sweetening agent (from about 0.01% to about 20%).

The term "lozenge" as used herein includes: breath mints, troches, pastilles, microcapsules, and fast-dissolving solid forms including freeze dried forms (cakes, wafers, thin films, tablets) and fast-dissolving solid forms including compressed tablets. The term "fast-dissolving solid form" as used herein means that the solid dosage form dissolves in less than about 60 seconds, preferably less than about 15 seconds, more preferably less than about 5 seconds, after placing the solid dosage form in the oral cavity. Fast-dissolving solid forms are disclosed in copending U.S. patent application Ser. No. 08/253,890, filed Jun. 3, 1994, Brideau; U.S. Pat. Nos. 4,642,903; 4,946,684; 4,305,502; 4,371,516; 5,188,825; 5,215,756; 5,298,261; 3,882,228; 4,687,662; 4,642,903. All of these patents are incorporated herein by reference in their entirety.

Lozenges include discoid-shaped solids comprising a therapeutic agent in a flavored base. The base may be a hard sugar candy, glycerinated gelatin or combination of sugar with sufficient mucilage to give it form. These dosage forms are generally described in Remington: The Science and Practice of Pharmacy, 19th Ed., Vol. II, Chapter 92, 1995. Lozenge compositions (compressed tablet type) typically include one or more fillers (compressible sugar), flavoring agents, and lubricants. Microcapsules of the type contemplated herein are disclosed in U.S. Pat. No. 5,370,864, Peterson et al., issued Dec. 6, 1994, which is herein incorporated by reference in its entirety.

In still another aspect, the invention comprises a dental implement impregnated with a composition comprising one or more host response modulating agent. The dental implement comprises an implement for contact with teeth and other tissues in the oral cavity, said implement being impregnated with a safe and therapeutically effective amount of host response modulating agent. The dental implement can be impregnated fibers including dental floss or tape, chips or strips and polymer fibers. Dental floss or tape typically comprise at least about 0.01 mg host response modulating agent per cm of material. The dental implement can also be a dental tool used for stimulating the periodontal tissue such as a toothpick or rubber tip.

Types of carriers or oral care excipients which may be included in compositions of the present invention, along with specific non-limiting examples, are:

Abrasives

Dental abrasives useful in the topical, oral carriers of the compositions of the subject invention include many different materials. The material selected must be one which is compatible within the composition of interest and does not excessively abrade dentin. Suitable abrasives include, for example, silicas including gels and precipitates, insoluble sodium polymetaphosphate, hydrated alumina, calcium carbonate, dicalcium orthophosphate dihydrate, calcium pyrophosphate, tricalcium phosphate, calcium polymetaphosphate, and resinous abrasive materials such as particulate condensation products of urea and formaldehyde.

Another class of abrasives for use in the present compositions is the particulate thermo-setting polymerized resins as described in U.S. Pat. No. 3,070,510 issued to Cooley & Grabenstetter on Dec. 25, 1962. Suitable resins include, for example, melamines, phenolics, ureas, melamine-ureas, melamine-formaldehydes, urea-formaldehyde, melamine-urea-formaldehydes, cross-linked epoxides, and cross-linked polyesters. Mixtures of abrasives may also be used.

Silica dental abrasives of various types are preferred because of their unique benefits of exceptional dental cleaning and polishing performance without unduly abrading tooth enamel or dentine. The silica abrasive polishing materials herein, as well as other abrasives, generally have an average particle size ranging between about 0.1 to about 30 microns, and preferably from about 5 to about 15 microns. The abrasive can be precipitated silica or silica gels such as the silica xerogels described in Pader et al., U.S. Pat. No. 3,538,230, issued Mar. 2, 1970, and DiGiulio, U.S. Pat. No. 3,862,307, issued Jan. 21, 1975, both incorporated herein by reference. Preferred are the silica xerogels marketed under the trade name "Syloid" by the W.R. Grace & Company, Davison Chemical Division. Also preferred are the precipitated silica materials such as those marketed by the J. M. Huber Corporation under the trade name, Zeodent®, particularly the silica carrying the designation Zeodent 119®. The types of silica dental abrasives useful in the toothpastes of the present invention are described in more detail in Wason, U.S. Pat. No. 4,340,583, issued Jul. 29, 1982. The abrasive in the toothpaste compositions described herein is generally present at a level of from about 6% to about 70% by weight of the composition. Preferably, toothpastes contain from about 10% to about 50% of abrasive, by weight of the composition.

A particularly preferred precipitated silica is the silica disclosed in U.S. Pat. No. 5,603,920, issued on Feb. 18, 1997; U.S. Pat. No. 5,589,160, issued Dec. 31, 1996; U.S. Pat. No. 5,658,553, issued Aug. 19, 1997; U.S. Pat. No. 5,651,958, issued Jul. 29, 1997, all of which are assigned to the Procter & Gamble Co. All of these patents are incorporated herein by reference in their entirety.

Mixtures of abrasives can be used. All of the above patents regarding dental abrasives are incorporated herein by reference. The total amount of abrasive in dentifrice compositions of the subject invention preferably range from about 6% to about 70% by weight; toothpastes preferably contain from about 10% to about 50% of abrasives, by weight of the composition. Solution, mouth spray, mouthwash and non-abrasive gel compositions of the subject invention typically contain no abrasive.

Sudsing Agents (Surfactants)

Suitable sudsing agents are those which are reasonably stable and form foam throughout a wide pH range. Sudsing agents include nonionic, anionic, amphoteric, cationic, zwitterionic, synthetic detergents, and mixtures thereof. Many suitable nonionic and amphoteric surfactants are disclosed by U.S. Pat. No. 3,988,433 to Benedict; U.S. Pat. No. 4,051,234, issued Sep. 27, 1977, and many suitable nonionic surfactants are disclosed by Agricola et al., U.S. Pat. No. 3,959,458, issued May 25, 1976, both incorporated herein in their entirety by reference.

a.) Nonionic and Amphoteric Surfactants

Nonionic surfactants which can be used in the compositions of the present invention can be broadly defined as compounds produced by the condensation of alkylene oxide groups (hydrophilic in nature) with an organic hydrophobic compound which may be aliphatic or alkyl-aromatic in nature. Examples of suitable nonionic surfactants include poloxamers (sold under trade name Pluronic), polyoxyethylene sorbitan esters (sold under trade name Tweens), fatty alcohol ethoxylates, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides, and mixtures of such materials.

The amphoteric surfactants useful in the present invention can be broadly described as derivatives of aliphatic secondary and tertiary amines in which the aliphatic radical can be a straight chain or branched and wherein one of the aliphatic substituents contains from about 8 to about 18 carbon atoms and one contains an anionic water-solubilizing group, e.g., carboxylate, sulfonate, sulfate, phosphate, or phosphonate. Other suitable amphoteric surfactants are betaines, specifically cocamidopropyl betaine. Mixtures of amphoteric surfactants can also be employed.

The present composition can typically comprise a nonionic, amphoteric, or combination of nonionic and amphoteric surfactant each at a level of from about 0.025% to about 5%, preferably from about 0.05% to about 4%, and most preferably from about 0.1% to about 3%.

b.) Anionic Surfactants

Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate and sodium coconut monoglyceride sulfonates are examples of anionic surfactants of this type. Other suitable anionic surfactants are sarcosinates, such as sodium lauroyl sarcosinate, taurates, sodium lauryl sulfoacetate, sodium lauroyl isethionate, sodium laureth carboxylate, and sodium dodecyl benzenesulfonate. Mixtures of anionic surfactants can also be employed. The present composition typically comprises an anionic surfactant at a level of from about 0.025% to about 9%, preferably from about 0.05% to about 7%, and most preferably from about 0.1% to about 5%.

Fluoride Ions

The present invention may also incorporate free fluoride ions. Preferred free fluoride ions can be provided by sodium fluoride, stannous fluoride, indium fluoride, and sodium monofluorophosphate. Sodium fluoride is the most preferred free fluoride ion. Norris et al., U.S. Pat. No. 2,946,725, issued Jul. 26, 1960, and Widder et al., U.S. Pat. No. 3,678,154 issued Jul. 18, 1972, disclose such salts as well as others. These patents are incorporated herein by reference in their entirety.

The present composition may contain from about 50 ppm to about 3500 ppm, and preferably from about 500 ppm to about 3000 ppm of free fluoride ions.

Thickening Agents

In preparing toothpaste or gels, it is necessary to add some thickening material to provide a desirable consistency of the composition, to provide desirable active agent release characteristics upon use, to provide shelf stability, and to provide stability of the composition, etc. Preferred thickening agents are carboxyvinyl polymers, carrageenan, hydroxyethyl cellulose, laponite and water soluble salts of cellulose ethers such as sodium carboxymethylcellulose and sodium carboxymethyl hydroxyethyl cellulose. Natural gums such as gum karaya, xanthan gum, gum arabic, and gum tragacanth can also be used. Colloidal magnesium aluminum silicate or finely divided silica can be used as part of the thickening agent to further improve texture.

A preferred class of thickening or gelling agents includes a class of homopolymers of acrylic acid crosslinked with an alkyl ether of pentaerythritol or an alkyl ether of sucrose, or carbomers. Carbomers are commercially available from B.F. Goodrich as the Carbopol® series. Particularly preferred carbopols include Carbopol 934, 940, 941, 956, and mixtures thereof.

Copolymers of lactide and glycolide monomers, the copolymer having the molecular weight in the range of from about 1,000 to about 120,000 (number average), are useful for delivery of actives into the periodontal pockets or around the periodontal pockets as a "subgingival gel carrier." These polymers are described in U.S. Pat. No. 5,198,220, Damani, issued Mar. 30, 1993, P&G, U.S. Pat. No. 5,242,910, Damani, issued Sep. 7, 1993, P&G, and U.S. Pat. No. 4,443,430, Mattei, issued Apr. 17, 1984, all of which are incorporated herein by reference.

Thickening agents in an amount from about 0.1% to about 15%, preferably from about 2% to about 10%, more preferably from about 4% to about 8%, by weight of the total toothpaste or gel composition, can be used. Higher concentrations can be used for chewing gums, lozenges (including breath mints), sachets, non-abrasive gels and subgingival gels.

Humectants

Another optional component of the topical, oral carriers of the compositions of the subject invention is a humectant. The humectant serves to keep toothpaste compositions from hardening upon exposure to air, to give compositions a moist feel to the mouth, and, for particular humectants, to impart desirable sweetness of flavor to toothpaste compositions. The humectant, on a pure humectant basis, generally comprises from about 0% to about 70%, preferably from about 5% to about 25%, by weight of the compositions herein. Suitable humectants for use in compositions of the subject invention include edible polyhydric alcohols such as glycerin, sorbitol, xylitol, butylene glycol, polyethylene glycol, and propylene glycol, especially sorbitol and glycerin.

Flavoring and Sweetening Agents

Flavoring agents can also be added to the compositions. Suitable flavoring agents include oil of wintergreen, oil of peppermint, oil of spearmint, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, thymol, linalool, cinnamaldehyde glycerol acetal known as CGA, and mixtures thereof. Flavoring agents are generally used in the compositions at levels of from about 0.001% to about 5%, by weight of the composition.

Sweetening agents which can be used include sucrose, glucose, saccharin, dextrose, levulose, lactose, mannitol, sorbitol, fructose, maltose, xylitol, saccharin salts, thaumatin, aspartame, D-tryptophan, dihydrochalcones, acesulfame and cyclamate salts, especially sodium cyclamate and sodium saccharin, and mixtures thereof. A composition preferably contains from about 0.1% to about 10% of these agents, preferably from about 0.1% to about 1%, by weight of the composition.

In addition to flavoring and sweetening agents, coolants, salivating agents, warming agents, and numbing agents can be used as optional ingredients in compositions of the present invention. These agents are present in the compositions at a level of from about 0.001% to about 10%, preferably from about 0.1% to about 1%, by weight of the composition.

The coolant can be any of a wide variety of materials. Included among such materials are carboxamides, menthol, ketals, diols, and mixtures thereof. Preferred coolants in the present compositions are the paramenthan carboxyamide agents such as N-ethyl-p-menthan-3-carboxamide, known commercially as "WS-3", N,2,3-trimethyl-2-isopropylbutanamide, known as "WS-23," and mixtures thereof. Additional preferred coolants are selected from the group consisting of menthol, 3-1-menthoxypropane-1,2-diol known as TK-10 manufactured by Takasago, menthone glycerol acetal known as MGA manufactured by Haarmann and Reimer, and menthyl lactate known as Frescolat® manufactured by Haarmann and Reimer. The terms menthol and menthyl as used herein include dextro- and levorotatory isomers of these compounds and racemic mixtures thereof. TK-10 is described in U.S. Pat. No. 4,459,425, Amano et al., issued Jul. 10, 1984. WS-3 and other agents are described in U.S. Pat. No. 4,136,163, Watson, et al., issued Jan. 23, 1979; the disclosure of both are herein incorporated by reference in their entirety.

Preferred salivating agents of the present invention include Jambu® manufactured by Takasago. Preferred warming agents include capsicum and nicotinate esters, such as benzyl nicotinate. Preferred numbing agents include benzocaine, lidocaine, clove bud oil, and ethanol.

Anticalculus Agent

The present invention also includes an anticalculus agent, preferably a pyrophosphate ion source which is from a pyrophosphate salt. The pyrophosphate salts useful in the present compositions include the dialkali metal pyrophosphate salts, tetraalkali metal pyrophosphate salts, and mixtures thereof. Disodium dihydrogen pyrophosphate ($Na_2H_2P_2O_7$), tetrasodium pyrophosphate ($Na_4P_2O_7$), and tetrapotassium pyrophosphate ($K_4P_2O_7$) in their unhydrated as well as hydrated forms are the preferred species. In compositions of the present invention, the pyrophosphate salt may be present in one of three ways: predominately dissolved, predominately undissolved, or a mixture of dissolved and undissolved pyrophosphate.

Compositions comprising predominately dissolved pyrophosphate refer to compositions where at least one pyrophosphate ion source is in an amount sufficient to provide at least about 1.0% free pyrophosphate ions. The amount of free pyrophosphate ions may be from about 1% to about 15%, preferably from about 1.5% to about 10%, and most preferably from about 2% to about 6%. Free pyrophosphate ions may be present in a variety of protonated states depending on a the pH of the composition.

Compositions comprising predominately undissolved pyrophosphate refer to compositions containing no more than about 20% of the total pyrophosphate salt dissolved in the composition, preferably less than about 10% of the total pyrophosphate dissolved in the composition. Tetrasodium pyrophosphate salt is the preferred pyrophosphate salt in these compositions. Tetrasodium pyrophosphate may be the anhydrous salt form or the decahydrate form, or any other species stable in solid form in the dentifrice compositions. The salt is in its solid particle form, which may be its crystalline and/or amorphous state, with the particle size of the salt preferably being small enough to be aesthetically acceptable and readily soluble during use. The amount of pyrophosphate salt useful in making these compositions is any tartar control effective amount, and is generally from about 1.5% to about 15%, preferably from about 2% to about 10%, and most preferably from about 3% to about 8%, by weight of the dentifrice composition.

Compositions may also comprise a mixture of dissolved and undissolved pyrophosphate salts. Any of the above mentioned pyrophosphate salts may be used.

The pyrophosphate salts are described in more detail in Kirk & Othmer, *Encyclopedia of Chemical Technology*, Third Edition, Volume 17, Wiley-Interscience Publishers (1982), incorporated herein by reference in its entirety, including all references incorporated into Kirk & Othmer.

Optional agents to be used in place of or in combination with the pyrophosphate salt include such known materials as synthetic anionic polymers, including polyacrylates and copolymers of maleic anhydride or acid and methyl vinyl ether (e.g., Gantrez), as described, for example, in U.S. Pat. No. 4,627,977, to Gaffar et al., the disclosure of which is incorporated herein by reference in its entirety; as well as, e.g., polyamino propoane sulfonic acid (AMPS), zinc citrate trihydrate, polyphosphates (e.g., tripolyphosphate; hexametaphosphate), diphosphonates (e.g., EHDP; AHP), polypeptides (such as polyaspartic and polyglutamic acids), and mixtures thereof Alkali Metal Bicarbonate Salt The present invention may also include an alkali metal bicarbonate salt. Alkali metal bicarbonate salts are soluble in water and unless stabilized, tend to release carbon dioxide in an aqueous system. Sodium bicarbonate, also known as baking soda, is the preferred alkali metal bicarbonate salt. The present composition may contain from about 0.5% to about 30%, preferably from about 0.5% to about 15%, and most preferably from about 0.5% to about 5% of an alkali metal bicarbonate salt.

Miscellaneous Carriers

Water employed in the preparation of commercially suitable oral compositions should preferably be of low ion content and free of organic impurities. Water generally comprises from about 5% to about 70%, and preferably from about 20% to about 50%, by weight of the composition herein. These amounts of water include the free water which is added plus that which is introduced with other materials, such as with sorbitol.

Titanium dioxide may also be added to the present composition. Titanium dioxide is a white powder which adds opacity to the compositions. Titanium dioxide generally comprises from about 0.25% to about 5% by weight of the dentifrice compositions.

Other optional agents include synthetic anionic polymeric polycarboxylates being employed in the form of their free acids or partially or preferably fully neutralized water soluble alkali metal (e.g. potassium and preferably sodium) or ammonium salts and are disclosed in U.S. Pat. No. 4,152,420 to Gaffar, U.S. Pat. No. 3,956,480 to Dichter et al., U.S. Pat. No. 4,138,477 to Gaffar, U.S. Pat. No. 4,183,914 to Gaffar et al., and U.S. Pat. No. 4,906,456 to Gaffar et al. Preferred are 1:4 to 4:1 copolymers of maleic anhydride or acid with another polymerizable ethylenically unsaturated monomer, preferably methyl vinyl ether (methoxyethylene) having a molecular weight (M.W.) of about 30,000 to about 1,000,000. These copolymers are available for example as Gantrez (AN 139 (M.W. 500,000), A.N. 119 (M.W. 250,000) and preferably S-97 Pharmaceutical Grade (M.W. 70,000), of GAF Corporation.

Composition Use

A safe and effective amount of the compositions of the present invention comprising a host response modulating agent may be topically applied to the mucosal tissue of the oral cavity, to the gingival tissue of the oral cavity, and/or to the surface of the teeth, for the treatment or prevention of the above mentioned diseases or conditions of the oral cavity, in several conventional ways. For example, the gingival or mucosal tissue may be rinsed with a solution (e.g., mouth rinse, mouth spray) containing the host response modulating agent; or if the host response modulating agent is included in a dentifrice (e.g., toothpaste, tooth gel or tooth powder), the gingival/mucosal tissue or teeth is bathed in the liquid and/or lather generated by brushing the teeth. Other non-limiting examples include applying a non-abrasive gel or paste, which contains the host response modulating agent, directly to the gingival/mucosal tissue or to the teeth with or without an oral care appliance described below; chewing gum that contains a host response modulating agent; chewing or sucking on a breath tablet or lozenge which contains a host response modulating agent. Preferred methods of applying the host response modulating agent ion to the gingival/mucosal tissue and/or the teeth are via rinsing with a mouth rinse solution and via brushing with a dentifrice. Other methods of topically applying the host response modulating agent ion to the gingival/mucosal tissue and the surfaces of the teeth are apparent to those skilled in the art.

The concentration of host response modulating agent in the composition of the present invention depends on the type of composition (e.g., toothpaste, mouth rinse, lozenge, gum, etc.) used to apply the host response modulating agent ion to the gingival/mucosal tissue and/or the teeth, due to differences in efficiency of the compositions contacting the tissue and teeth, and due also to the amount of the composition generally used. The concentration may also depend on the disease or condition being treated.

It is preferred that the mouth rinse to be taken into the oral cavity have a concentration of host response modulating agent in the range of from about 0.04% to about 0.4%, with from about 0.075% to about 0.2% more preferred and from about 0.1% to about 0.2%, by weight of the composition, even more preferred. Preferably mouth rinse compositions of the present invention deliver 3.75 to 22.5 mg of host response modulating agent to the oral cavity when approximately 15 ml of the rinse is used.

Mouth sprays preferably have host response modulating agent concentrations from about 0.15% to about 4%, with from about 0.2% to about 4% more preferred, with from about 0.75% to about 2%, by weight of the composition, even more preferred.

Preferably for dentifrices (including toothpaste and tooth gels) and non-abrasive gels, the concentration of host response modulating agent is in the range of from about 0.4% to about 4.5%, by weight of the composition, with from about 0.75% to about 3% preferred, and from about 1.5% to about 2%, by weight of the composition, even more preferred.

Chewing gums and lozenges (including breath mints), are generally formulated into compositions of individual unit size preferably containing from about 0.1 mg to about 12 mg, preferably from about 1 mg to about 6 mg, of host response modulating agent ion, per unit used in the oral cavity (i.e. per stick of gum, lozenge, breath mint, etc.).

For the method of promoting whole body health by treating and preventing diseases or conditions of the oral cavity, including breath malodor, of the present invention, a safe and effective amount of the active host response modulating agent is preferably applied to the gingival/mucosal tissue and/or the teeth (for example, by rinsing with a mouthrinse, directly applying a non-abrasive gel with or without a device, applying a dentifrice or a tooth gel with a toothbrush, sucking or chewing a lozenge or breathmint, etc.) preferably for at least about 10 seconds, preferably from about 20 seconds to about 10 minutes, more preferably from about 30 seconds to about 60 seconds. The method often involves expectoration of most of the composition following such contact. The frequency of such contact is preferably from about once per week to about four times per day, more preferably from about thrice per week to about three times per day, even more preferably from about once per day to about twice per day. The period of such treatment typically ranges from about one day to a lifetime. For particular oral care diseases or conditions the duration of treatment depends on the severity of the oral disease or condition being treated, the particular delivery form utilized and the patient's response to treatment. If delivery to the periodontal pockets is desirable, such as with the treatment of periodontal disease, a mouthrinse can be delivered to the periodontal pocket using a syringe or water injection device. These devices are known to one skilled in the art. Devices of this type include "Water Pik" by Teledyne Corporation. After irrigating, the subject can swish the rinse in the mouth to also cover the dorsal tongue and other gingival and mucosal surfaces. In addition a toothpaste, non-abrasive gel, toothgel, etc. can be brushed onto the tongue surface and other gingival and mucosal tissues of the oral cavity.

The present compositions may also be delivered to tissues and/or spaces within the oral cavity using electromechanical devices such as metering devices, targeted application devices and cleaning or integrated oral hygiene systems.

For treating oral tissue wounds and aiding tissue regeneration, fluid subgingival gel compositions that can be inserted via syringe and either a needle or catheter directly into the areas needing treatment, such as the periodontal cavities, are very useful and convenient. Preferred gel-like fluid compositions are those that transform into near solid phase in the presence of aqueous fluid such as water or crevicular fluid, such gels typically comprising from 0.02% to 6% of the active agent in a carrier system comprising a poly(lactyl-co-glycolide) copolymer and solvent such as propylene carbonate.

The hardened composition is thus retained at the site of application, and since the polymeric carrier undergoes slow degradation via hydrolysis, the host response modulating agent and any other active agent continue to release in a sustained manner from such compositions.

Pet care products such as foods, chews and toys are generally formulated to contain from 0.2 mg to 200 mg host response modulating agent per unit of product to be administered to the animal. The active agent can be incorporated for example, into a relatively supple but strong and durable material such as rawhide, ropes made from natural or synthetic fibers, and polymeric articles made from nylon, polyester or thermoplastic polyurethane. As the animal chews, licks or gnaws the product, chlorite and any other incorporated active elements are released into the animal's oral cavity into a salivary medium, comparable to an effective brushing or rinsing. Pet food embodiments can be formulated to provide from 0.2 mg to 200 mg active agent per feeding or treating session. The active agent can be incorporated as an ingredient or ad mixed into a pet food such as for example, a kibbled, semimoist, or canned food. Highly preferred food embodiments include carriers that tend to increase residence time of the food in the oral cavity. For example, the active agent can be incorporated in a carrier that will tend to stick or adhere to the teeth, in order that a certain amount of product will remain in the mouth and not be ingested immediately. The present compositions may also be incorporated into other pet care products including nutritional supplements and drinking water additives.

It should be understood that the present invention relates not only to methods for delivering the present chlorite containing compositions to the oral cavity of a human, but also to methods of delivering these compositions to the oral cavity of other animals, e.g., household pets or other domestic animals, or animals kept in captivity. Other animals include for example, dogs, cats or horses.

For dual- or multi-phase compositions the above concentrations of active agent represent the concentration of active agent after the phases are mixed together, which is usually just prior to use by the consumer. Thus, the concentration of active agent in the active-containing phase will vary depending on the amount of the second or additional phases to be mixed with the active-containing phase to obtain the final product for use.

The following non-limiting examples further describe preferred embodiments within the scope of the present invention. The examples are given solely for illustration and are not to be construed as limitations of this invention as many variations thereof are possible without departing from the spirit and scope thereof.

All percentages used herein are by weight of the composition unless otherwise indicated.

EXAMPLES

The following examples are made by conventional processes by mixing the following ingredients.

| Examples 1 and 2 Dentifrices | | |
|---|---|---|
| Ingredients | Example 1 (Wt. %) | Example 2 (Wt. %) |
| Sorbitol | 42.00 | 35.00 |
| Saccharin Sodium | 0.40 | 0.40 |

-continued

Examples 1 and 2 Dentifrices

| Ingredients | Example 1 (Wt. %) | Example 2 (Wt. %) |
|---|---|---|
| FD&C Blue (1% soln) | — | 0.05 |
| Precipitated Silica | 20.00 | 25.00 |
| Sodium Fluoride | 0.24 | 0.24 |
| Flavor | 1.00 | 1.50 |
| Sodium Alkyl Sulfate (27.9% Sol'n) | 4.00 | 1.20 |
| Trisodium Phosphate | 1.45 | — |
| Monosodium Phosphate | 0.59 | — |
| Carbopol 940 | 0.40 | 0.40 |
| Xanthan Gum | 0.50 | 0.70 |
| Titanium Dioxide | 1.00 | — |
| Cimetidine | 2.00 | — |
| Mifentidine | — | 0.50 |
| Purified Water | q.s. | q.s. |

Example 3

Oral Care Compositions

| Ingredient | Ex. 3A | Ex. 3B | Ex. 3C | Ex. 3D | Ex. 3E | Ex. 3F |
|---|---|---|---|---|---|---|
| Ketorolac Tromethamine | 0.10 | 0.01 | | | | |
| Cimetidine | | | | | 0.30 | |
| Famotidine | | | 2.50 | | | |
| Nizatidine | | | | 4.00 | | |
| N-hydroxy-2-[[diphenyl phosphinyl](2-phenylethyl)-amino]-acetamide | | | | | | 3.00 |
| Ethanol | 12.00 | 15.00 | | | 12.00 | 10.00 |
| Sorbitol | | | 37.20 | 37.20 | | |
| Polyethylene Glycol 600 | | | 3.00 | 3.00 | | |
| Glycerin | 10.00 | 12.00 | 19.00 | 19.00 | 10.00 | 12.00 |
| Dibasic Sodium Phosphate Heptahydrate | 0.07 | 0.48 | | | 0.07 | |
| Saccharin Sodium | 0.08 | 0.08 | 0.17 | 0.17 | 0.08 | 0.050 |
| Monobasic Sodium Phosphate Monohydrate | 2.03 | 1.82 | 5.00 | 5.00 | 2.03 | |
| Polysorbate 80 | 0.33 | 0.33 | | | 0.33 | |
| FD&C Blue (1% Soln) | 0.02 | 0.02 | | | 0.05 | 0.04 |
| Sodium Alkyl Sulfate | | | 1.00 | 1.00 | | 0.080 |
| Carboxymethylcellulose | | | 0.30 | 0.30 | | |
| Flavor | 0.15 | 0.15 | 0.90 | 0.90 | 0.15 | 0.10 |
| Titanium Dioxide | | | 0.50 | 0.50 | | |
| Fumed Silica | | | 2.00 | 2.00 | | |
| Precipitated Silica | | | 20.00 | 20.00 | | |
| Sodium Fluoride | | | 0.24 | 0.24 | | 0.05 |
| Domiphen Bromide | | | | | 0.005 | |
| Cetylpyridinium Chloride | | | | | 0.045 | |
| Benzoic Acid | | | | | | 0.05 |
| Sodium Hydroxide (50% Sol'n) | | | | | | 0.20 |
| Purified Water | qs | qs | qs | qs | qs | qs |

Example 4

An example of a controlled-release polymer composition for placement in a periodontal pocket is as follows:

| Ingredients | (Wt. %) |
|---|---|
| Ethyl Cellulose, Type N22 from Hercules, Inc. | 88 |
| Mifentidine | 12 |

The ethyl cellulose is dissolved in chloroform and then the mifentidine is added. The resulting mixture is cast on a glass plate. After evaporation of the chloroform, the residual film is removed from the plate and cut into pieces.

Example 5

An example of a putty-like controlled-release composition for placement in a periodontal pocket is made by mixing the following:

| Ingredients | (Wt. %) |
|---|---|
| Calcium Stearate | 40 |
| Dextran | 29 |
| Castor Oil | 28 |
| Nizatidine | 3 |

Example 6

Subjects diagnosed to have both periodontitis and systemic blood levels of the acute phase reactant C reactive protein which are significantly increased over normal blood levels are entered into a clinical trial and assigned to either a group using a placebo dentifrice or a dentifrice containing 0.5% of the H-2 antagonist cimetidine. The subjects use their respective dentifrices daily for a period of six months. Analysis of blood samples taken at baseline before initiation of the study's treatment phase and again following six months of products usage for levels of the acute phase reactant C-reactive protein shows a significant decrease in the blood levels of C-reactive protein for subjects using the cimetidine dentifrice as compared to the placebo group.

Example 7

Subjects diagnosed to have both periodontitis and significantly elevated systemic blood levels of the apolipoprotein B associated with blood LDL levels are entered into a clinical trial and randomly assigned to either a group using a placebo dentifrice or a dentifrice containing 0.35% of the H-2 antagonist ranitidine. Subjects use their respective dentifrices daily for a period of six months. Analysis of blood samples taken at baseline before initiation of the study's treatment phase and again following six months of products usage, for levels of the apolipoprotein B shows a significant decrease for the subjects using the ranitidine dentifrice as compared to the placebo group.

Example 8

Sub-Gingival Gels

| Ingredient | Ex. 8A | Ex. 8B |
|---|---|---|
| Cimetidine | 10.0 | |
| Ranitidine | | 12.0 |
| Poly(lactyl-co-glycolide)/ 50:50 copolymer | 30.0 | 20.0 |
| Propylene carbonate | 60.0 | 68.0 |
| Total | 100.0 | 100.0 |

The above compositions can be prepared by first dissolving the copolymer into the propylene carbonate using a propeller mixer. Powdered drug active is slowly added and mixed into the polymeric solution to a uniform consistency. The resulting gel like fluids can be inserted into or around the periodontal pocket or gingival region via syringe.

Having thus described the invention in detail, it will be clear to those skilled in the art that various changes may be made without departing from the scope of the invention and the invention is not to be considered limited to what is described in the specification.

What is claimed is:

1. A topical oral care composition for controlling oral cavity bacterial infection and reducing risk of developing an oral bacteria-induced systemic disease in human and other animal subjects, said composition consisting essentially of:
    a) a safe and effective amount of a combination of anti-oxidant and H2-antagonist host-response modulating agents, wherein the anti-oxidant is selected from one or a mixture of gallic acid, N-acetyl cysteine, or anethole dithiolthione and the H2-antagonist is selected from one or a mixture of cimetidine, etintidine, ranitidine, tiotidine, lupitidine, donetidine, famotidine, roxatidine, pifatidine, lamtidine, zaltidine, nizatidine, mifentidine, ramixotidine, loxtidine, bisfentidine, sufotidine, ebrotidine, or impromidine,
    b) a safe and effective amount of an additional oral therapeutic active selected from one or a mixture of antimicrobial/antiplaque agents selected from benzalkonium chloride, salicylanilide, domiphen bromide, cetylpyridinium chloride, tetradecylpyridinium chloride, and N-tetradecyl-4-ethylpyridinium chloride, and
    c) a pharmaceutically acceptable oral carrier.

2. A topical oral care composition according to claim 1 in a form selected from a mouthrinse, toothpaste, tooth gel, tooth powder, non-abrasive gel, chewing gum, mouth spray, lozenge, dental implement, and a pet care product.

* * * * *